(12) United States Patent
Wang et al.

(10) Patent No.: US 12,702,663 B2
(45) Date of Patent: Aug. 11, 2026

(54) AUTOMATED ASSESSMENT OF WOUND TISSUE

(71) Applicant: ASTRAZENECA AB, Södertälje (SE)

(72) Inventors: Yinhai Wang, Cambridge (GB); Adrian Mark Freeman, Cambridge (GB)

(73) Assignee: AstraZeneca AB, Södertälje (SE)

( * ) Notice: Subject to any disclaimer, the term of this patent is extended or adjusted under 35 U.S.C. 154(b) by 261 days.

(21) Appl. No.: 18/252,698

(22) PCT Filed: Nov. 11, 2021

(86) PCT No.: PCT/EP2021/081422

§ 371 (c)(1),
(2) Date: May 11, 2023

(87) PCT Pub. No.: WO2022/101361

PCT Pub. Date: May 19, 2022

(65) Prior Publication Data

US 2024/0005501 A1 Jan. 4, 2024

(30) Foreign Application Priority Data

Mar. 26, 2021 (EP) .................................... 21165361

(51) Int. Cl.
*G06K 9/00* (2022.01)
*A61B 5/00* (2006.01)
(Continued)

(52) U.S. Cl.
CPC ........ *A61K 31/4545* (2013.01); *A61B 5/0066* (2013.01); *A61B 5/445* (2013.01);
(Continued)

(58) Field of Classification Search
CPC .............. A61K 31/4545; A61K 9/0053; A61K 31/573; A61K 45/06; A61B 5/0066;
(Continued)

(56) References Cited

U.S. PATENT DOCUMENTS

2016/0284084 A1 9/2016 Gurcan et al.
2020/0193597 A1 6/2020 Fan et al.
2021/0137912 A1* 5/2021 Tiganescu .............. A61K 45/06

FOREIGN PATENT DOCUMENTS

WO WO-2008053194 A2 5/2008
WO WO-2018217162 A1 * 11/2018 ............. A61B 5/015
(Continued)

OTHER PUBLICATIONS

Armstrong, D.G., et al., "Validation of a Diabetic Wound Classification System: The contribution of depth, infection, and ischemia to risk of amputation," Diabetes Care 21:855-859, American Diabetes Association, United States (May 1998).
(Continued)

*Primary Examiner* — Xin Jia
(74) *Attorney, Agent, or Firm* — Sterne, Kessler, Goldstein & Fox P.L.L.C.

(57) ABSTRACT

A method of assessing a wound in a subject is provided. The method comprises obtaining one or more optical coherence tomography images of the wound and analysing the one or more optical coherence tomography images using a deep learning model that has been trained to classify pixels in an optical coherence tomography image of a wound between a plurality of classes comprising a plurality of classes associated with different types of wound tissue, thereby obtaining for each image analysed, an indication of the location of tissue likely to belong to each of the different types of wound tissue in the respective image.

21 Claims, 20 Drawing Sheets

(51) Int. Cl.

| | |
|---|---|
| ***A61K 9/00*** | (2006.01) |
| ***A61K 31/4545*** | (2006.01) |
| ***A61K 31/573*** | (2006.01) |
| ***A61K 45/06*** | (2006.01) |
| ***A61P 17/02*** | (2006.01) |
| ***G06T 7/00*** | (2017.01) |
| ***G06T 7/55*** | (2017.01) |
| ***G06T 7/60*** | (2017.01) |
| ***G06V 10/764*** | (2022.01) |

(52) U.S. Cl.

CPC .......... *A61K 9/0053* (2013.01); *A61K 31/573* (2013.01); *A61K 45/06* (2013.01); *A61P 17/02* (2018.01); *G06T 7/0014* (2013.01); *G06T 7/55* (2017.01); *G06T 7/60* (2013.01); *G06V 10/764* (2022.01); *G06T 2207/10101* (2013.01); *G06T 2207/20081* (2013.01); *G06T 2207/20084* (2013.01); *G06T 2207/30088* (2013.01); *G06V 2201/03* (2022.01)

(58) Field of Classification Search

CPC ..... A61B 5/445; A61B 5/0073; A61B 5/7267; A61P 17/02; A61P 3/10; G06T 7/0014; G06T 7/55; G06T 7/60; G06T 2207/10101; G06T 2207/20081; G06T 2207/20084; G06T 2207/30088; G06V 10/764; G06V 2201/03; G16H 15/00; G16H 30/40; G16H 50/20; A61L 2300/432; A61L 26/0066

See application file for complete search history.

(56) References Cited

FOREIGN PATENT DOCUMENTS

| | | | | |
|---|---|---|---|---|
| WO | WO-2020148721 A1 * | 7/2020 | .......... A61B 5/1079 |
| WO | WO-2020217644 A1 * | 10/2020 | ............ G06N 20/00 |
| WO | WO-2021094390 A1 | 5/2021 | |
| WO | WO-2022101361 A2 | 5/2022 | |

OTHER PUBLICATIONS

ClinicalTrials.gov, "Glucocorticoids and Skin Healing in Diabetes (GC-SHealD) (GC-SHealD)," Identifier NCT03313297, accessed at https://clinicaltrials.gov/study/NCT03313297?term=NCT03313297&rank=1, accessed on Jun. 27, 2023, 12 pages.

Deegan, A.J., et al., "Optical coherence tomography angiography monitors human cutaneous wound healing over time," Quant. Imaging Med. Surg. 8(2):135-150, AME Publishing Company, Hong Kong (Mar. 2018).

Dolz, J., et al., "Dense multi-path U-Net for ischemic stroke lesion segmentation in multiple image modalities, " in Brainlesion: Glioma, Multiple Sclerosis, Stroke and Traumatic Brain Injuries, Part 1, pp. 271-282, International MICCA Brainlesion Workshop, Springer, United Kingdom (2018).

Glinos, G.D., et al., "Optical coherence tomography for assessment of epithelialization in a human ex vivo wound model," Wound Repair and Regeneration 25(6):1017-1026, Wound Healing Society, United States (Nov. 2017).

Goodfellow, I.J., et al., "Generative Adversarial Nets," Proceedings of the International Conference on Neural Information Processing Systems, pp. 2672-2680 (Dec. 2014).

Greaves, N.S., et al., "Skin substitute-assisted repair shows reduced dermal fibrosis in acute human wounds validated simultaneously by histology and optical coherence tomography," Wound Rep. Reg. 23(4):483-494, Wiley, United States (2015).

Greaves, N.S., et al., "Optical coherence tomography: a reliable alternative to invasive histological assessment of acute wound healing in human skin?" Br. J. Dermatol. 170(4):840-850, Oxford Academic Press, United Kingdom (Apr. 2014).

International Search Report and Written Opinion for International Application No. PCT/EP2021/081422 mailed Feb. 17, 2022, 19 pages.

Kazeminia, S., et al., "GANs for medical image analysis," Artificial Intelligence in Medicine 109:101938, pp. 1-40, Elsevier, Netherlands (Sep. 2020).

Li, S., et al., "Imaging in Chronic Wound Diagnostics," Advances in Wound Care 9(5):245-263, Mary Ann Liebert, Inc., United States (May 2020).

Marijanovic, D, and Filko, D., "A Systematic Overview of Recent Methods for Non-Contact Chronic Wound Analysis," Applied Sciences 10(21):7613, pp. 1-28 Multidisciplinary Digital Publishing Institute, Switzerland (Oct. 2020).

Mukherjee, R., et al., "Automated Tissue Classification Framework for Reproducible Chronic Wound Assessment," BioMed Research International, 2014:851582, pp. 1-9, Hindawi Publishing Corporation, United Arab Emirates (Jul. 2014).

NICE.org, "Diabetic foot problems: prevention and management NICE guideline," accessed at www.nice.org.uk/guidance/ng19, accessed Jun. 27, 2023, published Aug. 26, 2015, last updated Oct. 11, 2019, 47 pages.

Ronneberger, O., et al., "U-Net: Convolutional Networks for Biomedical Image Segmentation," in Medical Image Computing and Computer-Assisted Intervention—MICCAI 2015, pp. 234-241, SpringerLink, United States (May 2015).

Sen, C.K., et al., "Human skin wounds: A major and snowballing threat to public health and the economy," Wound Repair Regen. 17(6):763-771, Wiley, United States (Nov. 2009).

Senn, B., et al., "Period Prevalence and Risk Factors for Postoperative Short-Term Wound Complications in Vulvar Cancer: A Cross-Sectional Study," International Journal of Gynecological Cancer 20(4):646-654, BMJ Journals, United Kingdom (May 2010).

Tulloch, J., et al., "Machine Learning in the Prevention, Diagnosis, and Management of Diabetic Foot Ulcers: A Systematic Review," IEEE Access 8:198977-199000, Institute of Electrical and Electronics Engineers, United States (Nov. 2020).

Wagh, A., et al., "Semantic Segmentation of Smartphone Wound Images: Comparative Analysis of AHRF and CNN-Based Approaches, " IEEE Access 8:181590-181604, Institute of Electrical and Electronics Engineers, United States (Aug. 2020).

Wang, Y., et al., "Volumetric quantification of wound healing by machine learning and optical coherence tomography in adults with type 2 diabetes: the GC-SHEALD RCT," medRxiv, pp. 1-18, Cold Spring Harbor Laboratory, United States (Jul. 2021).

Yeh, A.T., et al., "Imaging wound healing using optical coherence tomography and multiphoton microscopy in an in vitro skin-equivalent tissue model," Journal of Biomedical Optics 9(2):248-253, SPIE—the International Society for Optical Engineering in cooperation with International Biomedical Optics Society, United States (Mar. 2004).

Zhang, Z., et al., "Translating and segmenting multimodal medical volumes with cycle- and shape-consistency generative adversarial network," Proceedings of the IEEE Conference on Computer Vision and Pattern Recognition, p. 9242-9251, Institute of Electrical and Electronics Engineers, United States (Feb. 2018).

Zhou, Z., et al., "UNet++: A Nested U-Net Architecture for Medical Image Segmentation," Deep Learning in Medical Image Analysis and Multimodal Learning for Clinical Decision Support 11045:3-11, Springer, Switzerland (Jul. 2018).

* cited by examiner

Biopsy=2, Treatment=2

AUTOMATED ASSESSMENT OF WOUND TISSUE

CROSS REFERENCE TO RELATED APPLICATIONS

This application is a 35 U.S.C. § 371 National Phase Application of International Application Number PCT/EP2021/081422, filed Nov. 11, 2021, which claims priority to International Application Number PCT/EP2020/081788, filed Nov. 11, 2020, and European Application Number EP 21165361.3, filed Mar. 26, 2021, each of which is incorporated by reference herein in its entirety.

FIELD OF THE INVENTION

The present invention relates to the automated analysis of wound tissue. In particular, the present invention relates to methods of assessing wounds by analysing optical coherence tomography (OCT) images of the wounds using a deep learning model.

BACKGROUND TO THE INVENTION

According to a 2010 paper (Senn et al, 2010), in 2009 chronic wounds to the skin affected 6.5 million people in the United States and led to $25 billion in annual treatment costs. One significant example of a patient population that experience delayed wound healing is the diabetic patient population. Rising rates of obesity and diabetes, combined with an aging population, leads to an expectation that the number of people affected by chronic wounds will continue to rise. Ineffective treatment of these wounds can result in infection, sepsis, amputation, and in the most extreme cases, death.

Wound healing is a dynamic, interactive process involving coagulation, inflammation, tissue formation and tissue remodelling. Currently, histological analysis of tissue biopsies is the gold standard for assessment and diagnosis of normal and pathological wounds, enabling the visualisation of the structural architecture of the wound tissue (Greaves et al., 2014). Biopsy is an invasive procedure that is associated with discomfort for the patient and complications such as scarring, infection, delay of the healing process. It is further unsuitable for the longitudinal monitoring of a particular wound site. Thus, in clinical practice, wounds are still primarily assessed by manual techniques such as visual inspection, photography and calliper measurement. These traditional techniques are inherently variable and limited. Imaging techniques have recently been investigated as possible alternatives to histopathology, in order to gain a more detailed and precise view of a wound in a non-invasive manner. Non-invasive options include digital camera imaging, optical coherence tomography (OCT), laser Doppler and molecular resonance imaging (MRI). These vary in their abilities, costs and feasibility of use.

OCT is a tomographic imaging technique that uses low-coherence light (typically infrared light) to capture images from within optical scattering media such as biological tissue. Interferometric detection of reflected light enables capture of micrometer resolution images of the tissue up to 2 mm deep (Greaves et al., 2014). In medical imaging, OCT is most commonly used to assess ocular conditions such as glaucoma and macular degeneration. OCT is particularly attractive in the context of wound assessment because it is non-invasive and only requires a handheld instrument placed in contact with the skin. However, the information that can be obtained from such images is currently still very limited, and either requires extensive manual expert assessment (e.g. to extract values such as epidermal thickness from manually selected images and regions), provides only crude information such as the mean grayscale value which has been shown to correlate with the amount of fibrosis (Greaves et al., 2015) or does not segment the wound tissue into individual sub-compartments, but instead merely segments a section of imaged skin into layers or "slabs" residing at specified depths from the skin surface (Deegan et al., 2018). These slabs are putatively referred to as the papillary dermis, lower papillary/upper reticular dermis, and reticular dermis layers, respectively. In the context of wound tissue, tissue epidermal layers may not be present and other tissue compartments such as blood clots, scabs and neoepidermal tissue can be found. The practical clinical utility of OCT for wound assessment is therefore still limited.

It is an object of the present disclosure to provide a new strategy for assessing wounds as described below, which could provide richer and less variable clinically relevant information in a practical clinical context.

SUMMARY OF THE INVENTION

The present inventors have devised a machine-learning based approach for automated analysis of wound tissue from optical coherence tomography images. The approach is applicable to all types of wounds, requires no manual input and is able to produce clinically relevant metrics for the assessment of wound healing. The method addresses the need for automating and enriching the assessment of wounds and wound healing, for example for improved monitoring of patients suffering from chronic wounds. Briefly, this is achieved at least in part by providing a machine learning model that is trained to identify and locate different tissue compartments present within a wound at variable depths, that were previously not identified in OCT images. In contrast to the prior art that simply uses depth of tissue as the deterministic factor to indicate layers (Deegan et al., 2018), the technique described herein involves image analysis of individual pixel values and inter-pixel relationships to indicate which sub-tissue compartment a pixel belongs to. No arbitrary correlation with tissue sub-compartment and tissue depth is used. The technique described herein allows for accurate measurement of the area (in mm 2) and 3D volume (in mm 3) of each sub-tissue compartment at and around the wound site that is not possible from prior art methods, such as those described in Deegan et al., 2018.

Accordingly, in a first aspect the present specification provides a method of assessing a wound in a subject, the method comprising analysing one or more optical coherence tomography images of the wound using a deep learning model that has been trained to classify pixels in an optical coherence tomography image of a wound between a plurality of classes comprising a plurality of classes associated with different types of wound tissue, thereby obtaining for each image analysed, an indication of the location of tissue likely to belong to each of the different types of wound tissue in the respective image. The present inventors have surprisingly discovered that a plurality of different types of wound tissue could be identified in OCT images of wounds using deep learning classifiers, and further that the accuracy of identification of wound tissue in OCT images of wounds by deep learning classifiers could be improved by including a plurality of classes corresponding to different types of wound tissues.

The plurality of classes associated with different types of wound tissue may comprise at least a class associated with neoepidermis, a class associated with clot tissue and a class associated with granulation tissue. Analysing the one or more optical coherence tomography images of the wound using the deep learning model may comprise obtaining for each image analysed an indication of the location of likely neoepidermis, likely clot tissue and likely granulation tissue in the respective image. The plurality of classes associated with different types of wound tissue may further comprise a class associated with collagen and/or a class associated with liquid blood. Analysing the one or more optical coherence tomography images of the wound using the deep learning model may further comprise obtaining for each image analysed an indication of the location of likely collagen and/or likely liquid blood in the respective image. The present inventors have further identified specific types of wound tissues which, if included as the classes of wound tissue types used to train a deep learning classifier to classify different types of tissues in POCT images would result in improved accuracy of classification of wound tissue. These include neoepidermis, clot, granulation tissue, collagen and liquid blood. The inventors have further identified that amongst these, neoepidermis, clot and granulation tissue had particular clinical significance and that it was therefore particularly advantageous to include these as part of the different types of wound tissue identified by the deep learning classifier.

The method may further comprise obtaining one or more optical coherence tomography images of the wound. The step of obtaining one or more optical coherence tomography (OCT) images may comprise receiving one or more OCT images, for example from a computing device, from an OCT image acquisition means, from a database, or from a user. Thus, the method may only comprise computer-implemented steps. In particular, the method may not include the step of acquiring one or more images of the wound using an OCT image acquisition means. The step of obtaining one or more OCT images may comprise acquiring one or more images of the wound using an OCT image acquisition means.

The deep learning model may provide as output a probability of each pixel belonging to each of the plurality of classes. In such cases, the indication of the location of tissue likely to belong to each of the different types of wound tissue may correspond to the areas comprising pixels that are assigned a probability above a respective predetermined threshold of belonging to the class associated with the respective wound tissue. For example, the indication of the location of likely neoepidermis, likely clot tissue and likely granulation tissue may correspond to the areas comprising pixels that are assigned a probability above a respective predetermined threshold of belonging to the class associated with neoepidermis, the class associated with clot tissue and the class associated with granulation tissue, respectively. The deep learning model may provide as output a single class label for each pixel. A single class label for each pixel may be obtained as the class that is associated with the highest probability amongst a set of probabilities for each class predicted by the deep learning model. In such cases, the indication of the location of tissue likely to belong to each of the different types of wound tissue may correspond to the areas comprising pixels that are assigned to the class associated with the respective type of wound tissue. For example, the indication of the location of likely neoepidermis, likely clot tissue and likely granulation tissue may correspond to the areas comprising pixels that are assigned to the class associated with neoepidermis, the class associated with clot tissue and the class associated with granulation tissue, respectively.

The plurality of classes may further comprise one or more classes selected from: a class associated with intact tissue, and a class associated with background. The plurality of classes may comprise or consist of classes associated with each of neoepidermis, clot tissue, granulation tissue, liquid blood, collagen, intact tissue and background. The inventors have further discovered that additional non-wound classes would further improve the accuracy of the classifier. The class associated with "background" may also be referred to as "void" or "outside". Such a class may encompass any area of the image that does not show either intact tissue or wound tissue, such as e.g. areas external to the surface of the skin, areas beyond the penetration depth of the imaging technique (e.g. beyond the depth at which the imaging technique has a desired resolution).

The deep learning model may have been trained using a plurality of training optical coherence tomography images, wherein areas of each training image showing visual features indicative of the presence of the different types of wound tissues are labelled accordingly. The labels associated with the training images may be referred to as "ground truth labels". For example, areas of the training images showing visual features indicative of the presence of neoepidermis, clot or granulation tissue may be labelled accordingly. Areas of the training images showing visual features indicative of the presence of intact tissue, collagen and blood may also be labelled accordingly. The ground truth labels may have been obtained by manual annotation by one or more experts. The plurality of training images may comprise at least 50 images, at least 60 images, at least 70 images, or at least images. The plurality of training images may have been selected to show a variety of wound tissue morphologies. The plurality of training images may have been subject to data augmentation as known in the art, prior to being used for training the deep learning model. For example, one or more of the plurality of training images may be subject to one or more pre-processing steps selected from: zooming, padding, jittering, flipping, etc. This may advantageously improve the performance of the deep learning model.

The deep learning model may take as input a single image and analysing the one or more optical coherence tomography images may comprise providing each of the one or more optical coherence tomography images individually as input to the deep learning model. The indication of tissue likely to belong to each of the different types of wound tissue, such as the location of likely neoepidermis, likely clot tissue and likely granulation tissue, in the respective image may be obtained as one or more segmentation maps, wherein a segmentation map is an image of the same size as the image analysed, with pixels classified in a particular class assigned a different value from pixels that have not been classified in the particular class. A separate segmentation map may be obtained for each class, each segmentation map having pixels classified in the respective class assigned one value (e.g. 1), and all other pixels assigned another value (e.g. 0). The optical coherence tomography images may be single colour images. The OCT images may be grayscale images. Each optical coherence tomography image of the wound may show signal from the surface of the skin of the subject to a maximum depth. The maximum depth may be between 1 and 2 mm. A plurality of optical coherence tomography images of the wound may be analysed and optionally obtained, together forming a stack of images that show signal across an area of the surface of the skin of the subject.

The area may have a diameter of between 5 and 10 mm. The area may be a square area of approximately 6×6 mm. The method may further comprise combining the indications of the location of the tissue likely to belong to each of the different types of wound tissue, such as the indication of the location of likely neoepidermis, likely clot tissue and likely granulation tissue, in the respective images to obtain a three-dimensional map of the location of tissue likely to belong to each of the different types of wound tissue, such as likely neopidermis, likely clot tissue and likely granulation tissue, in the wound.

The deep learning model may be a convolutional neural network. The deep learning network may be a u-net or a generative adversarial network. The deep learning network may comprise a contracting path that reduces spatial information and increases feature information, and an expansive path that combines features and spatial information. The contracting path may comprise convolution layers followed by ReLU and max pooling layers, and the expansive path may comprise a sequence of up-convolutions and concatenations with features from the contracting path. The deep learning model may be a convolutional neural network (CNN) comprising 58 layers. The deep learning model may be a CNN comprising a plurality of convolution layers, a plurality of ReLu (rectified linear unit) layers, a plurality of max pooling layers, and a plurality of depth concatenation layers. The CNN may further comprise a softmax layer that takes as input the output of the final convolution layer and produces as output a probability of each pixel of an image belong to each of a plurality of classes. The CNN may further comprise a pixel classification layer that assigns each pixel to a class. Reference to a deep learning model may in practice refer to the use of a single trained model or an ensemble of models, the output of which is combined to obtain an indication of the location of tissue likely to belong to each of the different types of tissue, such as likely neoepidermis, likely clot tissue and likely granulation tissue (and further optionally any other class used), in an image that is analysed by each of the deep learning models in the ensemble.

The images may be normalised before being provided as input to the deep learning model. Instead or in addition to this, the deep learning model may be a convolutional neural network comprising an image input layer in which an input image is normalised. Input images may be normalised using zerocenter normalisation, in which images are normalised to have a mean of 0 and a standard deviation of 1. Other normalisation procedures suitable for use in the context of digital image processing may be used, such as e.g. linear normalisation or non-linear normalisation. The method may further comprise applying one or more post-processing steps to the output of the deep learning model. The post-processing steps may comprise one or more of: smoothing the boundaries of the areas comprising pixels identified as belonging to one or more classes, and re-labelling pixels identified as belonging to one or more classes where the pixels satisfy one or more criteria applying to the neighbouring pixels. The criteria applying to the neighbouring pixels may comprise a minimum number of direct neighbours being assigned to the same class. For example, pixels that do not have at least a predetermined number of direct neighbours assigned to the class of the pixel may be relabelled. The new label may be chosen as a function of the labels assigned to the neighbouring pixels. This process may advantageously enable removal of isolated pixels, which may for example be relabelled to match the label that is most prominent in the area of the isolated pixel. The criteria applying to the pixel forming part of a group of neighbouring pixels and assigned to the same class, the group having a minimum size. For example, groups of neighbouring pixels that do not have a minimum size may be relabelled. The new label may be chosen as a function of the labels assigned to the pixels that surround the group of pixels. This may advantageously enable the removal of small islands of pixels, which may for example be relabelled to match the label of the pixels surrounding the "small island". The smoothing of the boundaries of the areas comprising pixels identified as belonging to one or more classes may be performed using Fourier descriptors, as known in the art. The smoothing of boundaries may be performed after any step of re-labelling pixels.

Analysing an optical coherence tomography image using the deep learning model may comprise obtaining a plurality of portions of the images, and analysing each portion with the deep learning model. The portions may be referred to as "tiles". The portions may be partially overlapping portions, or may each correspond to a different area of the original image. The plurality of portions may together recapitulate the entire original image. The method may further comprise combining the output of the deep learning model for each of the plurality of portions. The method may further comprise determining, using the output from the deep learning model, the surface area corresponding to the pixels identified by the deep learning model as likely to belong to at least one of the different types of wound tissue in the respective image. The method may comprise determining one or more of: the surface area corresponding to the pixels identified by the deep learning model as likely neoepidermis, the surface area corresponding to the pixels identified by the deep learning model as likely clot tissue, the surface area corresponding to the pixels identified by the deep learning model as likely granulation tissue, in at least one of the one or more images.

Where additional classes are used, the method may further comprise determining, using the output from the deep learning model, the surface area corresponding to the pixels identified by the deep learning model as likely to belong to a respective additional class. A surface area may be measured in $mm^2$. By contrast, an area in an image may correspond to a particular set of pixels. The surface area that corresponds to a set of pixels (an area) in an image may be obtained based on a known relationship between the size of pixels in an image and the size of the physical structures imaged.

The method may further comprise determining the volume of at least one of the different types of wound tissue in the wound, such as one or more of: the volume of neoepidermis in the wound, the volume of clot tissue in the wound, and the volume of granulation tissue in the wound by: analysing a plurality of images of optical coherence tomography images of the wound using the deep learning model; determining, using the output form the deep learning model, for each of the plurality of images, the surface area corresponding to the pixels identified as likely to belong to the respective one of the different types of wound tissue, such as the surface area corresponding to the pixels identified as likely neoepidermis, the surface area corresponding to the pixels identified by the deep learning model as likely clot tissue, and/or the surface area corresponding to the pixels identified by the deep learning model as likely granulation tissue; and multiplying the determined surface area(s) in each image by a predetermined distance. The predetermined distance may be the same for all images or may be different. The method may further comprise summing the volumes obtained from each image. The predetermined distance may correspond to a distance that separates areas of the wounds shown on the plurality of images. In other words, the plurality of images may each show an area of the wound that is separated from the area shown in a subsequent image in the plurality of images by a predetermined distance. Thus, multiplying the surface area of corresponding to the pixels in an image identified as likely showing a particular tissue compartment by the predetermined distance between said image and the next image in a plurality of images analysed may provide an estimate of the volume of tissue in the particular compartment between the two images.

The method may further comprise determining the ratio of the volume of at least one of the different types of wound tissue from a plurality of images, by dividing the volume by a corresponding volume determined from the same image(s) based on the area between the surface of the skin in the image and a predetermined depth from the surface. Instead or in addition to this, the method may further comprise determining the ratio of the surface area of at least one of the different types of wound tissue from an image, by dividing the surface area by a corresponding surface area determined from the same image(s) based on the area between the surface of the skin in the image and a predetermined depth from the surface. The surface of the skin may be the highest coordinate of any area of the image identified as not outside/background. The volume/surface area determined from the same image(s) based on the area between the surface of the skin in the image and a predetermined depth from the surface may be referred to as "total volume/surface area" (or total tissue volume/surface area). The total volume/surface area may be obtained as the volume/surface area between the top of the image and a 1 mm penetration depth from the surface of the skin, excluding any volume/surface area classified as "outside" and "blood (liquid)". The predetermined depth may be chosen based on the resolution of the image. The predetermined depth may be between 0.5 mm and 2 mm. The predetermined depth may be chosen from: 0.5 mm, mm, 0.7 mm, 0.8 mm, 0.9 mm. 1 mm, 1.1 mm, 1.2 mm, 1.3 mm, 1.4 mm, or 1.5 mm. The present inventors have found a depth of 1 mm to be particularly suitable.

The method may comprise determining the volume of neoepidermis, the volume of clot and/or the volume of granulation tissue in the wound, and/or one or more of the corresponding ratios. These metrics have been identified as having particular clinical significance in the assessment of wound healing. The method may further comprise determining the width of the wound based on a dimension of the location(s) of tissue identified as likely to belong to one or more of the different types of wound tissue in at least one of the one or more images, optionally wherein the one or more of the different types of wound tissue include neoepidermis, clot and granular tissue. The one or more of the different types of wound tissue may further include collagen. Determining the width of the wound in an image may comprise determining the width of a continuous location of tissue identified as likely to belong to one or more of the different types of wound tissue in the image, where the width is the largest dimension of said tissue along an axis perpendicular to the depth axis in the image. In other words, the width of a wound may be identified as the length of the longest straight line along an axis perpendicular to the depth axis in the image, the line extending between two points identified as likely to belong to the one or more of the different types of wound tissues and not crossing any location that is identified as not likely to belong to any of the one or more of the different types of wound tissues. An axis that is parallel (or as close as possible to parallel) to the surface of the skin may be used instead of an axis that is perpendicular to the depth axis in the image. Determining the width of the wound may comprise determining a width of the wound by analysing each of a plurality of images of the wound, and identifying the width of the wound as the maximum width determined across the plurality of images.

The subject may be a human subject. The wound may be a skin wound. The wound may be a traumatic wound, a surgical wound, or a skin ulcer.

In a second aspect, the present specification provides a method of providing a tool for assessing a wound in a subject, the method comprising: obtaining a plurality of training optical coherence tomography images of wounds, wherein each image is associated with labels indicating the areas of images showing visual features indicative of the presence of a plurality of different types of wound tissues; and using the plurality of training optical coherence tomography images of wounds, training a deep learning model to classify pixels in an optical coherence tomography image of a wound between a plurality of classes comprising a plurality of classes associated with the different types of wound tissue, thereby obtaining for each image analysed, an indication of the location of tissue likely to belong to each of the different types of wound tissue in the respective image.

The method of the present aspect may have any of the features described in relation to the first aspect.

The method of the first and second aspect are computer-implemented.

In a third aspect, the present specification provides a system for automated assessment of wound tissue, the system comprising: at least one processor, and at least one non-transitory computer readable medium containing instructions that, when executed by the at least one processor, cause the at least one processor to perform operations comprising: receiving one or more optical coherence tomography images of a wound; and analysing the one or more optical coherence tomography images using a deep learning model that has been trained to classify pixels in an optical coherence tomography image of a wound between a plurality of classes comprising a plurality of classes associated with different types of wound tissue, thereby obtaining for each image analysed, an indication of the location of tissue likely to belong to each of the different types of wound tissue in the respective image. The system according to the present aspect may be configured to implement the method of any embodiment of the first aspect. In particular, the at least one non-transitory computer readable medium may contain instructions that, when executed by the at least one processor, cause the at least one processor to perform operations comprising any of the operations described in relation to the first aspect. The system according to the present aspect may additionally be configured to implement the method of any embodiment of the second aspect. In particular, the at least one non-transitory computer readable medium may contain instructions that, when executed by the at least one processor, cause the at least one processor to perform operations comprising any of the operations described in relation to the second aspect.

In a fourth aspect, the present specification provides system for providing a tool for automated assessment of wounds, the system comprising: at least one processor, and at least one non-transitory computer readable medium containing instructions that, when executed by the at least one processor, cause the at least one processor to perform operations comprising: receiving a plurality of training optical coherence tomography images of wounds, wherein each image is associated with labels indicating the areas of images showing visual features indicative of the presence of a plurality of different types of wound tissues; and using the plurality of training optical coherence tomography images of wounds, training a deep learning model to classify pixels in an optical coherence tomography image of a wound between a plurality of classes comprising a plurality of classes associated with the different types of wound tissue, thereby obtaining for each image analysed, an indication of the location of tissue likely to belong to each of the different types of wound tissue in the respective image. The system according to the present aspect may be configured to implement the method of any embodiment of the second aspect. In particular, the at least one non-transitory computer readable medium may contain instructions that, when executed by the at least one processor, cause the at least one processor to perform operations comprising any of the operations described in relation to the second aspect.

The system of the third or fourth aspect may further comprise optical coherence tomography imaging means in communication with the processor.

According to a fifth aspect, there is provided a method for monitoring a wound in a patient, the method comprising assessing the wound using the method of any embodiment of the first aspect. The method may comprise assessing the wound at a first time point and at least a further time point, using the method of any embodiment of the first aspect. The method may further comprise comparing one or more metrics (e.g. area and/or volume and/or volume ratio of one or more types of wound tissue) derived from the assessment at the first time point and at least one further time point, for example to establish the progression of wound healing between the first and at least one further time point. The method may comprises adjusting a course of treatment of the patient depending on the results of the assessment of the wound. The method may comprise administering or recommending for administration a compound or composition for the treatment of wounds, such as e.g. AZD4017 (as described in WO2008/053194, for example used as described in PCT/EP2020/081788) or a pharmaceutically acceptable salt thereof.

According to a sixth aspect, there is provided a method for the treatment or prophylaxis of wounds in a patient in need thereof, for example a patient susceptible to develop chronic wounds, comprising assessing the wound using the method of any embodiment of the first aspect. The method may comprise repeating the step of assessing the wound of the patient after a period of time and/or after administering to said patient a therapeutically effective amount of a compound or composition for the treatment of wounds. The method may comprises adjusting a course of treatment of the patient depending on the results of the assessment of the wound. A compound or composition for the treatment of wounds may be or comprise AZD4017 (as described in WO2008/053194, for example used as described in PCT/EP2020/081788) or a pharmaceutically acceptable salt thereof.

In embodiments of the methods of the fifth or sixth aspect, the patient may be a patient diagnosed with diabetes mellitus. The patient may be undergoing treatment for this condition. The diabetes may be type 1 or type 2 diabetes. The patient may be a human patient. The patient may be a human patient being treated with a glucocorticoid therapy, i.e. a patient being treated with a steroidal anti-inflammatory drug such as prednisolone or a human patient with an age of over 60 years, for example a patient that is 70, 75 or 80 years old. The patient may be a patient with a surgical or traumatic wound. The method may comprise adjusting a course of treatment of the patient depending on the results of the assessment of the wound. For example, if the comparison of one or more metrics derived from the assessment at different time points indicate that the wound healing is not progressing or not sufficiently progressing, the course of treatment may be changed such as e.g. by increasing the dose of a compound or composition for the treatment of wounds.

Also described is a compound or composition for use in a method for the treatment or prophylaxis of wounds in a patient in need thereof, the method comprising assessing a wound of the patient using the method of any embodiment of the first aspect. The method may further comprise repeating the step of assessing the wound of the patient after a period of time and/or after administering to said patient a therapeutically effective amount of the compound or composition for the treatment of wounds. The compound or composition may be or comprise AZD4017 (as described in WO2008/053194, for example used as described in PCT/EP2020/081788) or a pharmaceutically acceptable salt thereof. The method may comprise comparing one or more metrics derived from the assessments at different time points. The patient may be a patient diagnosed with diabetes mellitus. The patient may be undergoing treatment for this condition. The diabetes may be type 1 or type 2 diabetes. The patient may be a human patient. The patient may be a human patient being treated with a glucocorticoid therapy, i.e. a patient being treated with a steroidal anti-inflammatory drug such as prednisolone or a human patient with an age of over 60 years, for example a patient that is 70, 75 or 80 years old. The patient may be a patient with a surgical or traumatic wound. The method may comprise adjusting a course of treatment of the patient depending on the results of the assessment of the wound. For example, if the comparison of one or more metrics derived from the assessment at different time points indicate that the wound healing is not progressing or not sufficiently progressing, the course of treatment may be changed such as e.g. by increasing the dose of a compound or composition for the treatment of wounds. The compound or composition may be administered alone or in combination with any other treatment (including but not limited to the administration of any other compound or composition).

According to a further aspect, there is provided a non-transitory computer readable medium comprising instructions that, when executed by at least one processor, cause the at least one processor to perform the method of any embodiment of the first and/or second and/or fifth and/or sixth aspect.

According to a further aspect, there is provided a computer program comprising code which, when the code is executed on a computer, causes the computer to perform the method of any embodiment of the first and/or second and/or fifth and/or sixth aspect.

BRIEF DESCRIPTION OF THE FIGURES

So that the disclosure may be better understood, the specification refers to the following figures.

DETAILED DESCRIPTION OF THE INVENTION

Figure 1:
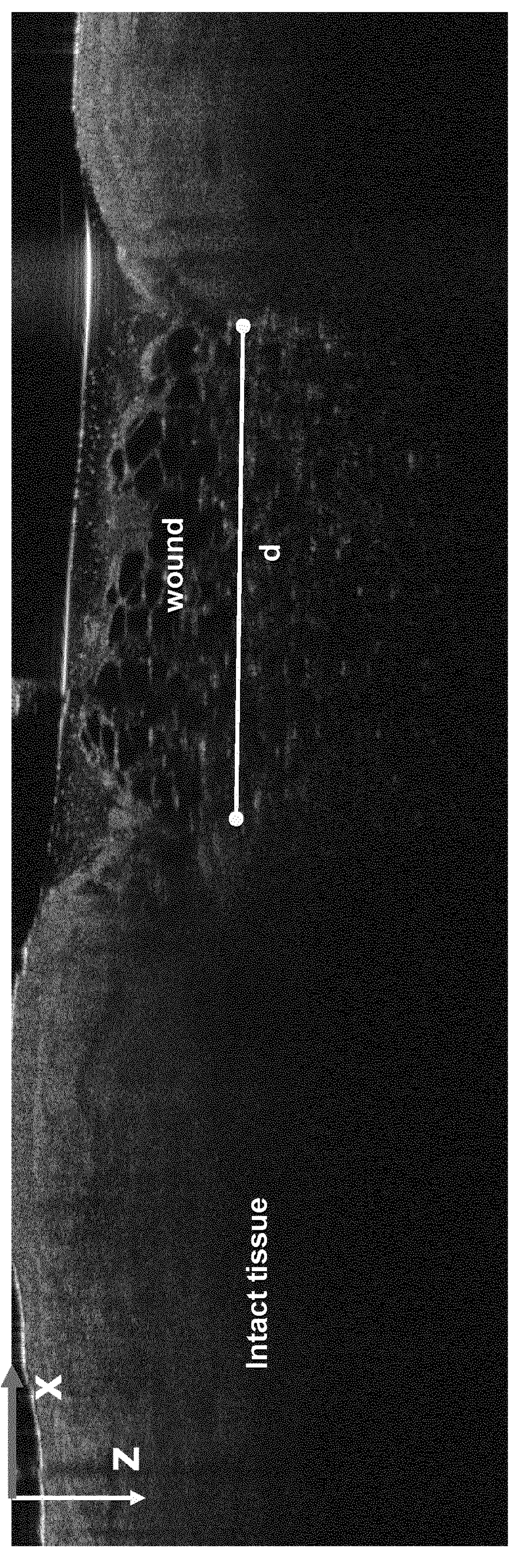
FIG. 1: Example of an OCT image of a wound.

Certain aspects and embodiments of the invention will now be illustrated by way of example and with reference to the figures described above.

In describing the present invention, the following terms will be employed, and are intended to be understood as indicated below.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

As used herein, the terms "computer system" includes the hardware, software and data storage devices for embodying a system or carrying out a method according to the above described embodiments. For example, a computer system may comprise a central processing unit (CPU), input means, output means and data storage, which may be embodied as one or more connected computing devices. Preferably the computer system has a display or comprises a computing device that has a display to provide a visual output display (for example in the design of the business process). The data storage may comprise RAM, disk drives or other computer readable media. The computer system may include a plurality of computing devices connected by a network and able to communicate with each other over that network. It is explicitly envisaged that computer system may consist of or comprise a cloud computer.

As used herein, the term "computer readable medium/media" includes, without limitation, any non-transitory medium or media which can be read and accessed directly by a computer or computer system. The media can include, but are not limited to, magnetic storage media such as floppy discs, hard disc storage media and magnetic tape; optical storage media such as optical discs or CD-ROMs; electrical storage media such as memory, including RAM, ROM and flash memory; and hybrids and combinations of the above such as magnetic/optical storage media.

As the skilled person understands, the complexity of the operations described herein (due at least to the amount of data that is analysed and the complexity of the machine learning models used) are such that they are beyond the reach of a mental activity. Thus, unless context indicates otherwise (e.g. where sample preparation or acquisition steps are described), all steps of the methods described herein are computer implemented.

The term "pharmaceutical composition" refers to a preparation which is in such form as to permit the biological activity of the active ingredient, and which contains no additional components which are unacceptably toxic to a subject to which the composition would be administered. Such compositions can be sterile. A pharmaceutical composition may comprise an active substance and at least one pharmaceutically acceptable excipient. The one or more pharmaceutically acceptable excipient(s) may be chosen from the group comprising fillers, binders, diluents and the like.

AZD4017 (also known as (S)-2-(1-(5-(cyclohexylcarbamoyl)-6-(propylthio)pyridin-2-yl)piperidin-3-yl)acetic acid) is a selective 11β-HSD1 inhibitor described in WO2008/053194 wherein full details of how the compound can be synthesised are to be found. AZD4017 may be provided in a pharmaceutically acceptable salt form. The use of AZD4017, or a pharmaceutically acceptable salt thereof, in the treatment or prophylaxis of wounds in a patient susceptible to develop chronic wounds, for example a diabetic patient, is described in co-pending application no. PCT/EP2020/081788.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. As used herein, treatment of wounds refers to an improvement in the wound healing process relative to that expected for the patient in the untreated state, i.e. relative to an untreated patient or a patient treated with placebo. As used herein, prophylaxis of wounds refers to treatment of patients susceptible to developing chronic wounds such that if they sustain a wound the chance that the wound will develop into a chronic wound is reduced relative that expected for the patient in the untreated state, i.e. relative to an untreated patient or a patient treated with placebo. The improvement in the wound healing process will typically entail a greater degree of wound healing over a given period of time i.e. the total time for a wound to heal or an increase in the rate at which the size of the wound reduces. The improvement in the wound healing process may, in addition, be evidenced by the quality of the skin either globally, or in and around the wound site, or the quality of the healing process. For example, prophylactic use of AZD4017 in the patient groups susceptible to developing chronic wounds would entail treatment of such patient with AZD4017 in order that should wounding occur the propensity to develop chronic wounds is reduced due to the ability of AZD4017 to accelerate the rate of wound closure and also improve skin properties such as its mechanical strength, promoting a thickening of the stratum corneum, thickening the epidermal layer, strengthening the corneal layer and skin hydration that are demonstrated in co-pending application no. PCT/EP2020/081788.

The terms "subject" and "patient" are used interchangeably. The subject may be mammalian (such as a cat, dog, horse, donkey, sheep, pig, goat, cow, mouse, rat, rabbit or guinea pig). Preferably, the subject is a human subject. In the context of the present disclosure, a patient may be a patient with a wound, or a patient that is prone to developing chronic wounds. Patient populations particular prone to developing chronic wounds include the diabetic patient population, who are prone to develop wounds such as diabetic foot ulcers that often lead to serious complications as described above. In addition, patients being treated with corticosteroids that typically experience thinning of the skin have an increased propensity to develop chronic wounds. Furthermore, elderly patients, particularly those with reduced skin hydration are also prone to developing wounds. Chronic wounds are wounds that have failed to proceed through an orderly and timely reparative process to produce anatomic and functional integrity of the injured site (Sen et al., 2010).

For the avoidance of doubt, reference to wounds throughout the specification refers to skin wounds. Thus, a wound is a break in cutaneous epithelial continuity characterised by disruption of structure and function of underlying tissues (Greaves et al., 2014). Skin wounds include surgical and traumatic wounds (including abrasions, superficial burns and incisions), as well as skin ulcers (such as e.g. pressure ulcers, foot and leg ulcers, etc.).

The terms "tissue compartment" (or "tissue component", "sub-tissue component", and "tissue type", all of which are used interchangeably) refer to tissue structures that are present in and around a wound, at one or more stages of the wound healing process. These may include the intact tissue surrounding the wound (which itself may comprise an epidermis component and a dermis component), and tissue that is part of the wound ("wound tissue compartment", "wound tissue component", "wound sub-tissue component", "wound tissue type", all of which are used interchangeably). Wound tissue types may include neoepidermis (also referred to as "neoepidermis"; epidermis newly formed during wound healing), granulation tissue (which as used herein refers to a tissue comprising extracellular matrix, fibroblasts and growing micro-vessels to allow blood perfusion; this component may be referred to herein as "granular tissue", "sponge tissue", "wound tissue with sponginess morphology" or "tissue with sponge morphology"), collagen (a component comprising mostly an extracellular matrix of type-II collagen, which may be referred to as "wound collagen"), clot (also referred to as "fibrin clot" or "wound clot"), and blood (liquid) (also simply referred to herein as "blood"). Blood vessels may also be visible, enabling capture of information regarding vascularization of the wound tissue. In particular, blood vessels may be captured in a separate channel such that these do not need to be segmented. In embodiments, this information is integrated with the information obtained using the methods described herein, for example by overlaying information from the blood vessel channel on one or more segmented images. An additional compartment that corresponds to any outside volume (void, volume external to the tissue, also referred to herein as "background") that may be visible on OCT images may be defined. In embodiments, the following tissue compartments may be distinguished in OCT images of wounds: neoepidermis, clot, granular tissue, collagen, intact tissue, blood (liquid) and outside (void or background).

Optical coherence tomography (OCT) refers to a tomographic imaging technique that uses light to capture micrometre to sub-micrometre resolution images from within optical scattering media such as biological tissue (e.g. skin). The method is based on low-coherence interferometry, typically employing near-infrared light. The use of relatively long wavelength light allows it to penetrate to a typical depth of 1-2 mm into the tissue. In embodiments, OCT images comprise a plurality of images (also referred to herein as "slices") of a structure which each capture a parallel plane (also referred to herein as "scanning planes" or "acquisition planes") extending over a predetermined maximum depth within a scanned area. The plurality of images acquired in a single acquisition may be referred to as a "stack". The plurality of images may be separated by a variable distance, for example to include more images within a certain range of a scanned area. Typically, the plurality of images are separated by a fixed distance. For example, a fixed or variable distance between 5 and 100 μm, between 10 and 100 μm, between 20 and 80 μm, between 30 and 70 μm, such as e.g. an interval (fixed or variable) chosen from: about 10 μm, about 20 μm, about 30 μm, about 40 μm, about 50 μm, about 60 μm, about 70 μm, about 80 μm, about 90 μm, and about 100 μm may be used. Suitably, a fixed distance of about 50 μm may be used. Alternatively, a fixed distance of about 100 μm may be used. As the skilled person understands, the distance between acquisition planes may be chosen as a compromise between the amount of additional information that can be obtained with increased resolution (i.e. decreasing the distance between acquisition planes), and the amount of data that can be conveniently acquired and analysed (which increases with the number of acquisition planes), bearing in mind the lateral resolution of the image acquisition process (typically a few μm, depending on the instrument). Each image may capture information from a single acquisition plane extending over a range of depth between 0 μm and a predetermined maximum depth. The maximum depth may be determined, for example, depending on one or more of: the expected depth of the structure(s) to be analysed, the desired minimum resolution of the images (where resolution is expected to decrease with increasing depth), the amount of data to be processed, the capabilities of the image acquisition system used, etc. For example, the maximum depth may be chosen from: a value between 0.5 and 2 mm, a value between 0.5 and 1.5 mm, a value between 0.5 and 1 mm, a value between 0.8 and 1.2 mm, about 0.5 mm, about 0.6 mm, about mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, or about 2 mm. Suitably, a maximum depth of about 1 mm may be chosen. The maximum depth may be the same as the native depth of the image acquisition system, or may be limited subsequent to image acquisition, for example by cropping the images to exclude data corresponding to a depth exceeding the predetermined maximum depth. For example, the depth that is visible in a raw image may be between 2-3 mm, but the resolution of the image acquisition system may only be guaranteed up to a depth of 1 mm. In embodiments, only data up to a depth equal to the depth up to which a desired resolution is maintained (e.g. the depth at which the image acquisition means has a guaranteed desired resolution) may be used, and this depth may be referred to as the "maximum depth". This depth may be smaller than the depth that is visible in the raw images. Each of the plurality of images is a two-dimensional image, the plurality of images together forming a three-dimensional representation of the imaged structure. Each one of the plurality of images may show structure visible on a particular plane extending over the depth coordinate. The depth coordinate may be referred to as the z coordinate, where x and y refer to orthogonal coordinates along the surface of the skin. For example, the y coordinate may be chosen as a scanning coordinate, such that each image shows data for a range of x-z coordinates at a particular y coordinate. In practice, a single image may cover a range of y coordinates depending on the lateral resolution of the imaging process), within a two dimensional visualisation field. A two dimensional visualisation field refers to an imaging area on the surface of the structure to be imaged (e.g. skin), which may be defined in x-y coordinates, and which is scanned to acquire a plurality of images showing parallel planes extending over a maximum depth. The dimensions of the two dimensional visualisation field is typically set by the features of the imaging system. A visualisation field may be an area of any geometry such as e.g. a square area, a rectangular area, and a circular area. The visualisation field may have a diameter of about 2 mm, about 3 mm, about 4 mm, about 5 mm, about 6 mm, about 7 mm, about 8 mm, about mm, between 4 and 10 mm, between 2 and 10 mm, or between 4 and 8 mm. The diameter of a visualisation field of arbitrary geometry may refer to the diameter of the largest circle that is completely included in the visualisation field. This may be equal to the diameter if the visualisation field is a circle, or to the length of the shortest vertex if the visualisation field is a square or rectangle. For example, a diameter of 6 mm may be used, with a circular visualisation field. As another example, a square visualisation field with dimensions of about 6×6 mm may be used, leading to a diameter of 6 mm (radius of 3 mm). In the context of imaging wounds, the diameter of the visualisation field may be seen as the diameter of the largest circular wound that could be completely imaged within said visualisation field. For example, when using an imaging system that has a visualisation field of 6 mm×6 mm, a circular wound of up to 3 mm radius can be completely imaged. Typically, OCT images are greyscale images. The distance between acquisition planes may be chosen such that a set number of images are acquired over a visualisation field. For example, a total of 120 images may be acquired over a scanning distance of 6 mm, with a fixed interval of 50 μm. An example of a single OCT image is shown on FIG. 1. On FIG. 1, the x and z dimensions are indicated, and the y dimension extends away from the page. The image shows data up to a depth (z axis) of approximately 2-3 mm (although the resolution of the image is only guaranteed up to 1 mm depth, in the apparatus that was used to acquire this image), along a width (x axis) of 6 mm. As can be seen on FIG. 1, the depth of tissue that is visible on a raw image may depend on the location of the void/tissue boundary. Similarly, the depth of tissue that is usable may depend on the location of the void/tissue boundary as well as the maximum depth that is used in the image (which maximum depth may depend e.g. on the image resolution as explained above).

Analysing Wound Images

Figure 2:
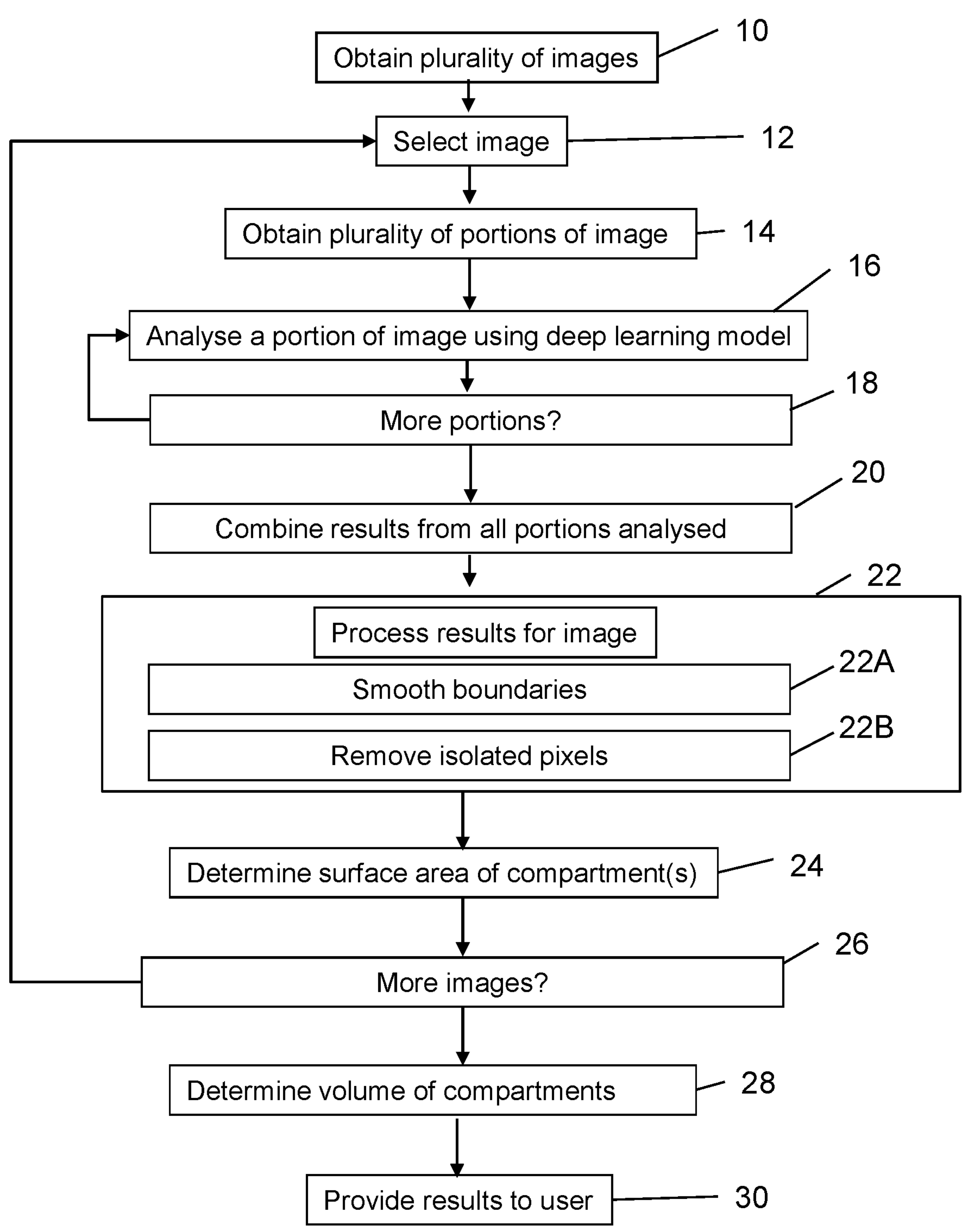
FIG. 2: Flowchart illustrating schematically a method of analysing wound tissue according to the disclosure.

The present disclosure provides method for assessing wounds, using OCT image data from the wound. An illustrative method will be described by reference to FIG. 2. In its simplest embodiment, the method comprises analysing (step 16) one or more optical coherence tomography images of a wound using a deep learning model that has been trained to classify pixels in an optical coherence tomography image of a wound between a plurality of classes comprising a plurality of classes associated with different types of wound tissue, thereby obtaining for each image analysed, an indication of the location of tissue likely to belong to each of the different types of wound tissue in the respective image. In the embodiment shown on FIG. 2, a plurality of optional steps are illustrated. In particular, the method may comprise obtaining a plurality of optical coherence tomography images of a wound (which can be referred to as a "stack" and each show a different area of the same wound along a scanning direction. The images may be obtained from a database, a computing device, a user, read from a computer readable medium, etc. In embodiments, the images may be obtained directly from an image acquisition means. At step 12, an image is selected from the stack. At step 14, a portion of the image is obtained (also referred to as a "tile"), and this is analysed by the deep learning model at step 16. Alternatively, the entire image can be analysed at step 16. Step 18 comprises checking whether all of the portions of the image have been analysed. If that is not the case, then step 16 is repeated for another portion, until all portions of the selected image have been analysed. At step 20, the results from all portions of the selected image that have been analysed are combined into a single result for the image. The results may comprise a class annotation for each pixel, which may be in the form of a segmentation map. The segmentation map may include annotations for all or a subset of the classes. For example, where a background class is used, this may not be included in the segmentation map for ease of visualisation. As another example, where an "intact tissue" class is used, this may not be included in the segmentation map for ease of visualisation. At step 22, the results of the analysis are post-processed, for example to remove isolated pixels and/or smooth the boundaries of areas annotated in the same class. This may result in a segmentation map that is easier to visualise and interpret. At step 24, the surface area corresponding to pixels that have been identified as belonging to at least one of the wound tissue classes is determined. This can be determined using a known relationship between the pixels in the image and the size of the corresponding physical area imaged. This step may be repeated for any tissue compartment of interest. At step 26, it is determined whether all of the images in the stack have been analysed. If that is not the case, steps 12-24 may be repeated for another image of the plurality of images, until all images have been analysed. Note that the order of steps 18-24 on FIG. 2 is for illustrative purposes only and other orders are possible. For example, all portions of all images may be analysed before steps 20-24 are performed. Alternatively, all portions of each image may be analysed and combined, before steps 22 and 24 are performed on each of the images. Steps 22 and 24 are preferably performed once the results from all portions of an image have been combined. Further, step 24 is preferably performed after step 22 has been performed, in other for the surface area determined to be in line with the data shown on the processed segmentation map. At step 28, the surface areas determined at step 24 for a plurality of images in the stack are used to determine the volume of tissue in at least one tissue compartment, in at least a portion of the stack of images. This may be obtained by multiplying the surface area determined for the tissue compartment in each image by the physical distance between the areas shown in the subsequent image in the plurality of images from which a volume is obtained. Typically, all images in the stack will be used. The distance between images in a stack is typically constant and determined by the parameters of the image acquisition means. Other metrics may be determined from the results of the deep learning analysis, such as e.g. the wound width, various combined surface areas, combined volumes, ratios of surface areas, ratios of volumes, etc. At step 30, the results are provided to a user. These may include one or more of: the segmentation maps, a combined (3D) visualisation of the segmentation maps, one or more metrics derived from the results of the deep learning analysis.

The methods of the present invention are performed on images of wound tissue, and are therefore in silico methods. In some embodiments, the methods may encompass the steps of obtaining information from a patient by acquiring OCT images of a wound of the patient, and analysing the images to identify, locate and optionally quantify a plurality of wound tissues within said images.

Systems

Figure 3:
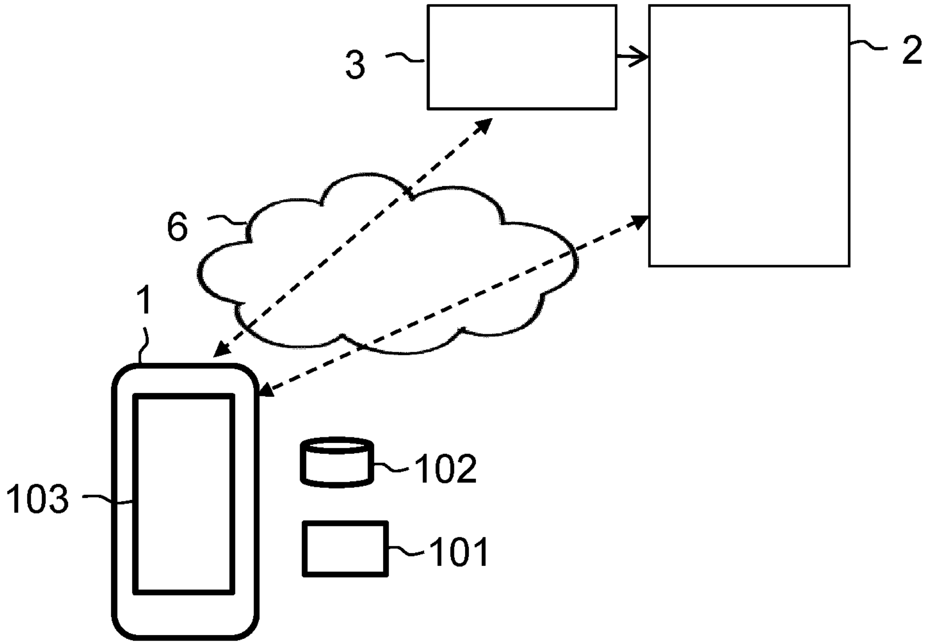
FIG. 3: Embodiment of a system for analysing wound tissue.

FIG. 3 shows an embodiment of a system for assessing wound tissue, according to the present disclosure. The system comprises a computing device 1, which comprises a processor 101 and computer readable memory 102. In the embodiment shown, the computing device 1 also comprises a user interface 103, which is illustrated as a screen but may include any other means of conveying information to a user such as e.g. through audible or visual signals. The computing device 1 is communicably connected, such as e.g. through a network 6, to OCT image acquisition means 3, such as an OCT system, and/or to one or more databases 2 storing image data. The computing device may be a smartphone, tablet, personal computer or other computing device. The computing device is configured to implement a method for analysing images, as described herein. In alternative embodiments, the computing device 1 is configured to communicate with a remote computing device (not shown), which is itself configured to implement a method of analysing images, as described herein. In such cases, the remote computing device may also be configured to send the result of the method of analysing images to the computing device. Communication between the computing device 1 and the remote computing device may be through a wired or wireless connection, and may occur over a local or public network such as e.g. over the public internet. The image data acquisition means may be in wired connection with the computing device 1, or may be able to communicate through a wireless connection, such as e.g. through a local or public network 6, as illustrated. The connection between the computing device 1 and the image data acquisition means 3 may be direct or indirect (such as e.g. through a remote computer). The OCT image data acquisition means 3 are configured to acquire OCT image data from wound tissue, for example from a skin wound of a patient.

Applications

The above methods find applications in a variety of clinical contexts. In particular, any clinical context in which the assessment of wound tissue is part of the clinical picture is likely to benefit from the present invention. For example, the above methods may be used in diagnosing and monitoring of dermatological disease or another disease associated with the presence of wounds, evaluation of response to treatment and intervention, and evaluation of wound healing and scar assessment. The use of OCT images advantageously means that the image acquisition process is non-invasive and without side effects, enabling longitudinal monitoring in all patient populations. Further, the entire method from image acquisition to analysis is fast (image acquisition taking typically less than a minute), with images analysed within seconds to minutes. This enables a rapid, reproducible, unbiased quantitative and qualitative characterisation of a wound and/or some of its compartments, with no expert medical involvement from acquisition to analysis. Further, the methods are reproducible, repeatable and accurate, which is not the case for the current clinical practice of visual assessment, or even with emerging research only practices making use of OCT images.

The examples below show the results of a clinical trial showing that administration of AZD4017 can improve the rate of wound healing in human diabetic patients, thus providing a new opportunity for the treatment or prophylaxis of patients at an elevated risk of developing chronic wounds. Development of wounds is particularly significant in diabetic patients, since such patients have a propensity to develop chronic wounds to the foot, or diabetic foot ulcers. Diabetic foot wounds can be categorised on the University of Texas diabetic wound classification system (Armstrong et al, Diabetes Care 1998; 21:855) and can lead to amputation, and even death, if complications arise. Criteria for the categorisation of the risk of developing a diabetic foot problem or needing an amputation are provided in the NICE Guidelines NG19 (Diabetic foot problems: prevention and management NICE guideline Published: 26 Aug. 2015 www.nice.org.uk/guidance/ng19). The NICE criteria for categorisation are based on an examination of a patient's foot for neuropathy, limb ischaemia, ulceration, callus, infection and/or inflammation, deformity, gangrene and Charcot arthropathy (see NG19 section 1.3.4). High risk patients are those who have suffered a) previous ulceration or b) previous amputation or c) on renal replacement therapy or d) neuropathy and non-critical limb ischaemia together or e) neuropathy in combination with callus and/or deformity or f) non-critical limb ischaemia in combination with callus and/or deformity. Patients with an active diabetic foot problem are defined as those with ulceration, spreading infection, critical limb ischaemia, gangrene, suspicion of an acute Charcot arthropathy, or an unexplained hot, red, swollen foot with, or without, pain. The NICE Guideline NG19 recommends that patients at high risk are evaluated very frequently—up to weekly evaluation is recommended at 1.3.11. Monitoring of wound healing (or lack thereof) is particularly important in assessing patients with such conditions, for example to assess whether a particular course of treatment is effective and/or to modify, adjust or recommend a new or existing course of treatment accordingly. The use of the methods of the present invention for this purpose is demonstrated herein, in particular to monitor the effects of AZD4017 administered orally to diabetic patients. In this context, the methods of the present invention provided evidence that AZD4017 administered orally to diabetic patients can deliver an improvement in the rate and extent of wound closure observed.

The specification also provides a method of treatment or prophylaxis of wounds comprising administration of an effective amount of a wound healing promoting course of treatment, for example administration of a drug such as e.g. AZD4017, to a patient in need thereof, the method further comprising assessing or monitoring a wound of the patient using the methods described herein. In such embodiments the patient in need thereof may be a diabetic patient, i.e. a patient with type 1 or type 2 diabetes. In such embodiments, the patient may be a patient that has been identified as being at moderate or high risk of developing a diabetic foot problem according to the NICE Guidance NG19. For example, as detailed above, the identification of the patient as at high risk may have been made on the basis that the patient a) has or previously has had ulceration or b) has had a previous amputation or c) has had renal replacement therapy or d) exhibits neuropathy and non-critical limb ischaemia together or e) exhibits neuropathy in combination with callus and/or deformity or f) exhibits non-critical limb ischaemia in combination with callus and/or deformity. Alternatively, the patient may be an elderly patient, i.e. a patient over the age of 60 years (for example over 70, 75 or 80 years old), or a patient being treated with glucocorticoids. Alternatively, the patient in need thereof may be a patient who has suffered a traumatic wound. Any such course of treatment can be used alone or in combination with further therapeutic agents. The further therapeutic agent may be selected from additional agents such as an immunomodulator, anti-inflammatories (e.g. glucocorticoids or NSAIDs), anti-allergic agents, pain relievers and combinations thereof. Drugs that promote wound healing, such as AZD4017 or a pharmaceutically acceptable salt thereof, may be administered via the oral route, in the form of pharmaceutical preparations comprising the active ingredient or a pharmaceutically acceptable salt or solvate thereof, or a solvate of such a salt, in a pharmaceutically acceptable dosage form. Depending upon the disorder and patient to be treated and the route of administration, the compositions may be administered at varying doses.

The following is presented by way of example and is not to be construed as a limitation to the scope of the claims.

EXAMPLES

Data

These examples show results acquired as part of a double-blind, randomized, parallel group, placebo-controlled phase II pilot trial investigating efficacy, safety and feasibility of 11β-hydroxysteroid dehydrogenase type 1 inhibition by AZD4017 to improve skin function and wound healing in patients with type 2 diabetes (T2DM) was performed (ClinicalTrials.gov Identifier: NCT03313297). This study involved oral twice daily administration of AZD4017 (400 mg per dose, n=14) or placebo (n=14) in human patients with T2DM. Study participants attended a screening visit and at days 0, 2, 7, 28, 30, 35 (=day of cessation of dosing of the investigational medicinal product (IMP)) and a follow-up visit at day 42.

To evaluate efficacy of oral AZD4017 on 24 hour 11B-HSD1 activity in skin, 3 mm punch biopsies were obtained at Visits 1 (day 0) and 4 (day 28) from lower outer forearm (midpoint between wrist and elbow) performed under local anaesthetic (e.g. lidocaine). This procedure was conducted by authorised trial personnel and did not require sutures. Both biopsies from visit 1 (day 0) and two biopsies from visit 4 (day 28) were imaged by OCT at Visits 2, 3, 5 and 6 as appropriate. The procedure takes approximately 2 minutes using a small probe applied to the skin. The procedure is non-invasive and pain-free. Optical coherence tomography (OCT) technology is practical for wound clinics due to the size of the equipment, portability and ease of use. The images are of high resolution regards the microstructure of the tissue, with limited depth analysis.

A total of 120 individual images (also referred to herein as "slices", together forming a "stack") per acquisition, spanning depths of 0 to 1 mm, and separated by a distance of 50 μm were acquired. Each image was 460×1378 pixels in size, covering a 6 mm×6 mm area acquired for a wound site with 3 mm radius, leading to over 76 million pixels or 200 MB of data per stack. Image files (including enrolment number, visit number and date) were stored on the OCT machine until the end of the trial, then transferred to a secure server, compiled, and analysed as will be described below. Each individual OCT image is grey coloured, with progressively lower contrast typically being observed in the OCT images obtained from areas further from the surface of the imaged media. There are also noise signals across the image. It can be difficult to identify areas of different morphology within an OCT image due to the novelty of OCT imaging, especially as some morphologies look very similar and are hard to differentiate by the untrained eye. Therefore there is a significant challenge for clinicians and scientists in understanding and analysing OCT images. Additionally, what qualifies as "wound tissue" as visible in an OCT image is not strictly defined and in practice encompasses a collection of non-intact tissue that may vary between clinicians making the assessment. This difficulty is further compounded by the large volume of images that need to be evaluated from a single patient, hindering the clinical usability of OCT imaging in dermatology. An OCT image stack can capture sublayers of the skin that undergo changes during the wounding and the wound healing process, and are critical to healing. However, due to the lack of expertise to analyse these, this information is not analysed. Instead, a crude analysis is performed in which a trained clinician arbitrarily selected one image of a stack as likely to show the largest wound diameter, and used simple image analysis tools to manually delineate the width of the wound and get a measurement for the wound diameter. These single measurements were entered into the case report form (CRF). An example of an OCT image on which such measurements were taken is shown in FIG. 1. FIG. 1 further shows the structures that were distinguished by the trained clinician for the purpose of determining an approximate wound diameter, labelled as "d".

Figure 4:
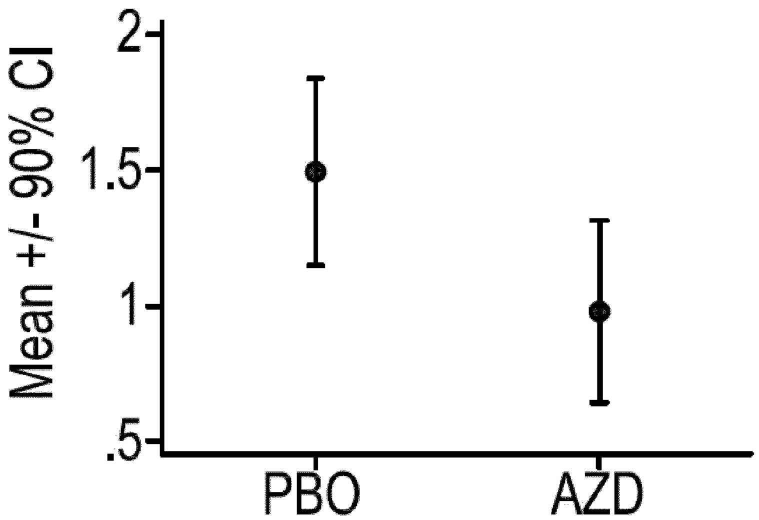
FIG. 4: Wound healing in placebo (PBO) and AZD4017 (AZD) treated cohorts as evidenced by wound gap diameter of wounds inflicted at days 0 and 28 at days 2 and 30, respectively. Confidence intervals for measurements are provided to right.
Figure 4:
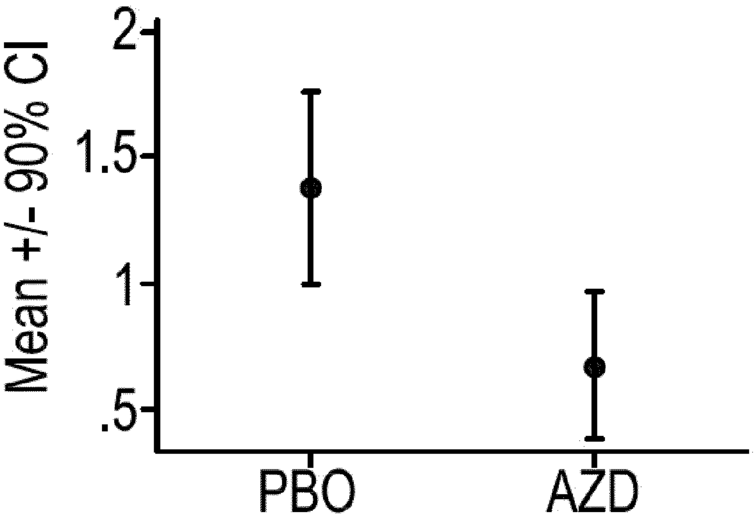

Examples of results from this study of wound healing using this relatively simple approach are presented in FIG. 4. The initial wounds created by puncture at days 0 and 28, respectively, were 3 mm in diameter. Treatment with AZD4017 (400 mg, twice daily oral) was initiated on day 0 and maintained for 35 days. At day 2 the wound gap diameter in the placebo arm and AZD4017 trial arms were compared and this comparison revealed a 35% improvement in the extent of healing in the treatment arm relative to placebo arm (mean wound gap diameter of 1.49 mm in placebo arm vs mm in AZD4017 treated arm). Thus administration of AZD4017 on the same day as the wound was inflicted delivered a significant improvement in the rate of wound healing.

However, as mentioned above, the present inventors realized that the OCT images contained a wealth of information that was not previously analysed. Additionally, the process of arbitrary selecting a single image in a stack, based on which wound diameter is assessed, is inherently subject to variability and lack of accuracy since different trained clinicians (or even the same clinician repeating an assessment) may not choose the same image, the delineation of the wound area is manual and subject to subjective criteria, and the image chosen may not in fact capture the maximum width of the wound. Thus, the inventors set out to develop a novel machine learning method to analyse OCT images, which has the potential to be applied to routine monitoring within clinical practice, and in addition preventative care for high risk patients. The aim of the methods developed were to enable the characterisation of the different areas of a wound, and monitoring physiological changes of the tissue compartments would allow health care staff engaged in wound better capability in the assessment and trajectory of an individual's wound over time. Using these methods, once the wound tissue regions are identified, a direct numerical measurement of the wound size can be obtained from a single image and from a stack of 120 slices of image from one sample. This approach advantageously removes the subjectivity in manual measurement of wound width and allows measurement of many images in a fast and automated manner. The digital image processing method therefore offers the potential for increased accuracy and higher sample throughput. Thus, a deep learning based image processing method was developed for recognising different sub-tissue components from optical coherence tomography (OCT) images.

Deep Learning Model and Training

Figure 5:
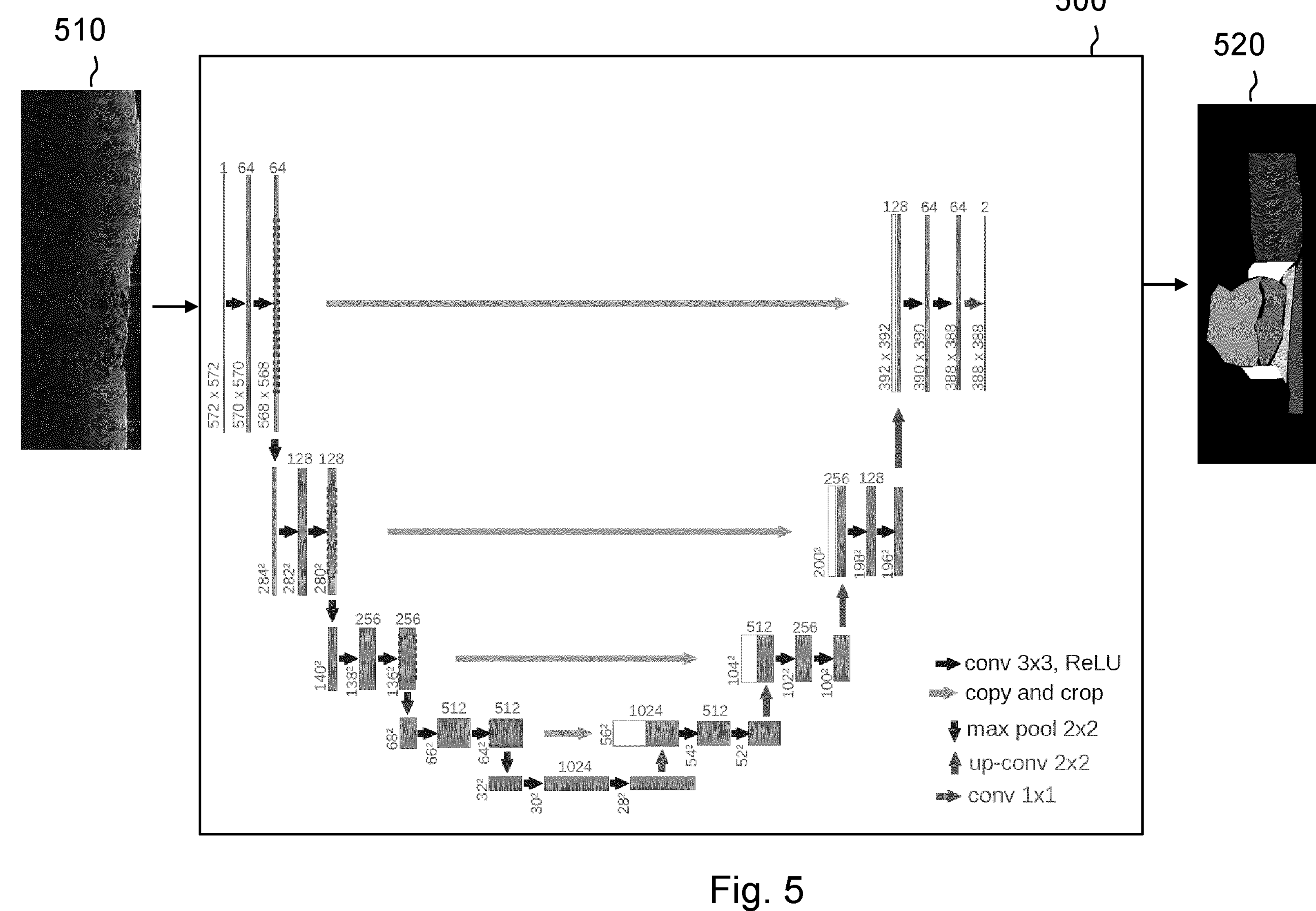
FIG. 5: Example deep learning architecture for analysis of wound tissue.

All models used herein were based on a u-net convolutional neural network (see Ronneberger O., Fischer P., & Brox T. (2015)). A u-net consists of a series of contracting operators which preserve important image features, and a sequence of upsampling operators which increase the image resolution to produce an output (image labels) that has the same size as the input image. FIG. 5 shows an exemplary architecture suitable for use herein. The deep learning model 500 (in this case, a u-net) takes as input a single OCT image 510, and produces as output a segmentation map 510. The segmentation map assigns a class identity one or more pixels in the original image. In the illustrated embodiment, pixels coloured in white are assigned a particular class identity (e.g.: class 1 or "wound tissue"). A segmentation map may in practice comprise a plurality of maps (also referred to as "masks"), each indicating which pixels belong to a particular class. For example, where the model classifies a pixel as belonging to one of 3 classes (outside, intact tissue, wound tissue), a segmentation map may be provided for each class, assigning a first value to all pixels in the respective class (e.g. a value of 1 may be assigned to all pixels classified as "outside" in the first segmentation map, to all pixels classified as "wound tissue" in the second segmentation map, and to all pixels classified as "intact tissue" in the third segmentation map), and a second value (e.g. 0) to all other pixels. Alternatively, segmentation maps assigned different values to each of a plurality of classes may also be used. Note that not all pixels have to be annotated in a segmentation map, i.e. a segmentation map may only identify pixels within one or more classes of interest, and essentially ignore all other pixels. Segmentation maps may be overlaid onto the original image (e.g. as contours or semi-transparent layers) to indicate the areas that have been labeled in each class for which a segmentation map is overlaid.

While FIG. 5 illustrates an embodiment with a u-net architecture, other architectures are possible and explicitly envisaged, such as e.g. generative adversarial networks (GANs, described in Goodfellow et al., 2014). In general, many deep learning architectures that are suitable for the segmentation of images may be suitable. U-nets or GANs are particularly useful examples of these. Thus, in particular, any variations of u-net and GANs deep learning architectures may be used, including U-net++(Zongwei et al., 2018), IVD-Net (Dotz Ben Ayed and Desrosiers, 2018), the architecture described in Zhang, Yang and Zheng (2018), and any of the architectures reviewed in Kazeminia et al. (2020). In the examples described below, a u-net architecture similar to that described in Ronneberger O., Fischer P., & Brox T. (2015) was used, as detailed in Table 1. The architecture was adapted to take as input a single colour image of size 256×256 pixels and to produce as output a segmentation map with n classes (where n varies depending on the embodiments described below, such as e.g. between n=3 and n=7). The model was fully trained based on the training data described (i.e. all parameters and coefficients of the model were trained, and no pre-trained parameters were used). Model training, assessment, and predictions using the trained model were all performed in Matlab (Matlab 9.7.0.1247435 (R2019b) Update 2). All statistical calculations and image post-processing was also done in Matlab.

As can be seen on Table 1, the model that was selected for the final clinical analysis consisted of 58 layers. The final segmentation layer output class labels in 7 categories (see below): 1. normal (intact tissue), 2. background (outside), 3. granulation tissue, 4. collagen, 5. blood, 6. neoepidermis, 7. clot.

TABLE 1

Architecture of a deep learning model suitable for use in the methods described herein. N = layer number. Each layer receives as a single input the output of the preceding layer unless indicated otherwise.

| N | Name | Function | Description |
|---|---|---|---|
| 1 | 'ImageInputLayer' | Image Input | 256 × 256 × 1 images with 'zerocenter' normalization |
| 2 | 'Encoder-Section-1-Conv-1' | Convolution | 64 3 × 3 × 1 convolutions with stride [1 1] and padding [1 1 1 1] |
| 3 | 'Encoder-Section-1-ReLU-1' | ReLU | ReLU |
| 4 | 'Encoder-Section-1-Conv-2' | Convolution | 64 3 × 3 × 64 convolutions with stride [1 1] and padding [1 1 1 1] |
| 5 | 'Encoder-Section-1-ReLU-2' | ReLU | ReLU-output provided to layer 6 and layer 51 |
| 6 | 'Encoder-Section-1-MaxPool' | Max Pooling | 2 × 2 max pooling with stride [2 2] and padding [0 0 0 0] |
| 7 | 'Encoder-Section-2-Conv-1' | Convolution | 128 3 × 3 × 64 convolutions with stride [1 1] and padding [1 1 1 1] |
| 8 | 'Encoder-Section-2-ReLU-1' | ReLU | ReLU |

TABLE 1-continued

Architecture of a deep learning model suitable for use in the methods described herein. N = layer number. Each layer receives as a single input the output of the preceding layer unless indicated otherwise.

| N | Name | Function | Description |
|---|---|---|---|
| 9 | 'Encoder-Section-2-Conv-2' | Convolution | 128 3 × 3 × 128 convolutions with stride [1 1] and padding [1 1 1 1] |
| 10 | 'Encoder-Section-2-ReLU-2' | ReLU | ReLU-output provided to layer 11 and layer 44 |
| 11 | 'Encoder-Section-2-MaxPool' | Max Pooling | 2 × 2 max pooling with stride [2 2] and padding [0 0 0 0] |
| 12 | 'Encoder-Section-3-Conv-1' | Convolution | 256 3 × 3 × 128 convolutions with stride [1 1] and padding [1 1 1 1] |
| 13 | 'Encoder-Section-3-ReLU-1' | ReLU | ReLU |
| 14 | 'Encoder-Section-3-Conv-2' | Convolution | 256 3 × 3 × 256 convolutions with stride [1 1] and padding [1 1 1 1] |
| 15 | 'Encoder-Section-3-ReLU-2' | ReLU | ReLU - output provided to layer 16 and layer 37 |
| 16 | 'Encoder-Section-3-MaxPool' | Max Pooling | 2 × 2 max pooling with stride [2 2] and padding [0 0 0 0] |
| 17 | 'Encoder-Section-4-Conv-1' | Convolution | 512 3 × 3 × 256 convolutions with stride [1 1] and padding [1 1 1 1] |
| 18 | 'Encoder-Section-4-ReLU-1' | ReLU | ReLU |
| 19 | 'Encoder-Section-4-Conv-2' | Convolution | 512 3 × 3 × 512 convolutions with stride [1 1] and padding [1 1 1 1] |
| 20 | 'Encoder-Section-4-ReLU-2' | ReLU | ReLU |
| 21 | 'Encoder-Section-4-DropOut' | Dropout | 50% dropout-output provided to layer 22 and layer 30 |
| 22 | 'Encoder-Section-4-MaxPool' | Max Pooling | 2 × 2 max pooling with stride [2 2] and padding [0 0 0 0] |
| 23 | 'Mid-Conv-1' | Convolution | 1024 3 × 3 × 512 convolutions with stride [1 1] and padding [1 1 1 1] |
| 24 | 'Mid-ReLU-1' | ReLU | ReLU |
| 25 | 'Mid-Conv-2' | Convolution | 1024 3 × 3 × 1024 convolutions with stride [1 1] and padding [1 1 1 1] |
| 26 | 'Mid-ReLU-2' | ReLU | ReLU |
| 27 | 'Mid-DropOut' | Dropout | 50% dropout |
| 28 | 'Decoder-Section-1-UpConv' | Transposed Convolution | 512 2 × 2 × 1024 transposed convolutions with stride [2 2] and cropping [0 0 0 0] |
| 29 | 'Decoder-Section-1-UpReLU' | ReLU | ReLU |
| 30 | 'Decoder-Section-1-DepthConcatenation' | Depth concatenation | Depth concatenation of 2 inputs (layer 29 and layer 21) |
| 31 | 'Decoder-Section-1-Conv-1' | Convolution | 512 3 × 3 × 1024 convolutions with stride [1 1] and padding [1 1 1 1] |
| 32 | 'Decoder-Section-1-ReLU-1' | ReLU | ReLU |
| 33 | 'Decoder-Section-1-Conv-2' | Convolution | 512 3 × 3 × 512 convolutions with stride [1 1] and padding [1 1 1 1] |
| 34 | 'Decoder-Section-1-ReLU-2' | ReLU | ReLU |
| 35 | 'Decoder-Section-2-UpConv' | Transposed Convolution | 256 2 × 2 × 512 transposed convolutions with stride [2 2] and cropping [0 0 0 0 ] |
| 36 | 'Decoder-Section-2-UpReLU' | ReLU | ReLU |
| 37 | 'Decoder-Section-2-DepthConcatenation' | Depth concatenation | Depth concatenation of 2 inputs (layer 36 and layer 15) |
| 38 | 'Decoder-Section-2-Conv-1' | Convolution | 256 3 × 3 × 512 convolutions with stride [1 1] and padding [1 1 1 1] |
| 39 | 'Decoder-Section-2-ReLU-1' | ReLU | ReLU |
| 40 | 'Decoder-Section-2-Conv-2' | Convolution | 256 3 × 3 × 256 convolutions with stride [1 1] and padding [1 1 1 1] |
| 41 | 'Decoder-Section-2-ReLU-2' | ReLU | ReLU |
| 42 | 'Decoder-Section-3-UpConv' | Transposed Convolution | 128 2 × 2 × 256 transposed convolutions with stride [2 2] and cropping [0 0 0 0] |
| 43 | 'Decoder-Section-3-UpReLU' | ReLU | ReLU |
| 44 | 'Decoder-Section-3-DepthConcatenation' | Depth concatenation | Depth concatenation of 2 inputs (layer 43 and layer 10) |
| 45 | 'Decoder-Section-3-Conv-1' | Convolution | 128 3 × 3 × 256 convolutions with stride [1 1] and padding [1 1 1 1] |
| 46 | 'Decoder-Section-3-ReLU-1' | ReLU | ReLU |
| 47 | 'Decoder-Section-3-Conv-2' | Convolution | 128 3 × 3 × 128 convolutions with stride [1 1] and padding [1 1 1 1] |
| 48 | 'Decoder-Section-3-ReLU-2' | ReLU | ReLU |
| 49 | 'Decoder-Section-4-UpConv' | Transposed Convolution | 64 2 × 2 × 128 transposed convolutions with stride [2 2] and cropping [0 0 0 0] |
| 50 | 'Decoder-Section-4-UpReLU' | ReLU | ReLU |
| 51 | 'Decoder-Section-4-DepthConcatenation' | Depth concatenation | Depth concatenation of 2 inputs (layer 50 and layer 5) |

TABLE 1-continued

Architecture of a deep learning model suitable for use in the methods described herein. N = layer number. Each layer receives as a single input the output of the preceding layer unless indicated otherwise.

| N | Name | Function | Description |
|---|---|---|---|
| 52 | 'Decoder-Section-4-Conv-1' | Convolution | 64 3 × 3 × 128 convolutions with stride [1 1] and padding [1 1 1 1] |
| 53 | 'Decoder-Section-4-ReLU-1' | ReLU | ReLU |
| 54 | 'Decoder-Section-4-Conv-2' | Convolution | 64 3 × 3 × 64 convolutions with stride [1 1] and padding [1 1 1 1] |
| 55 | 'Decoder-Section-4-ReLU-2' | ReLU | ReLU |
| 56 | 'Final-ConvolutionLayer' | Convolution | 7 1 × 1 × 64 convolutions with stride [1 1] and padding [0 0 0 0] |
| 57 | 'Softmax-Layer' | Softmax | Softmax |
| 58 | 'Segmentation-Layer' | Pixel Classification Layer | Cross-entropy loss with 'Normal', 'Background', and 5 other classes |

The models take as input a slice of scanned 2D OCT image (one colour, one channel) and perform the segmentation image into one or more components (see next section). In the implementations used to obtain the results below, each 460×1378 pixels image was divided into a plurality of 256×256 images (also referred to as "tiles"), each of which was analysed separately by the deep learning algorithm. The resulting segmentation maps were then combined to obtain an equivalent 460×1378 pixels segmentation map. This was performed for practical reasons only (due to the size of the input expected by the particular network used). Other sizes of tiles are possible, as well as not using tiles at all (e.g. analyzing an entire single OCT image). Additionally, the size of the input image provided to the deep learning model can be reduced by down-sampling (i.e. reducing the resolution of the image), rather than analyzing tiles separately.

Each model was trained using 84 single colour channel images of wounds (each 460×1324 pixels in size) chosen manually from over 318 stacks (each stack comprising 120 images of a single patient sample) from an anonymized set of 28 patients. The 84 images therefore represented 0.22% of all the images available in the study. The training images were chosen to capture a variety of morphologies. Alternative approaches could be used, such as using all data available or selecting data to include a balance of images obtained from the treatment and placebo groups. Each model was trained until a maximum number of epochs was reached (although other stopping criteria are possible and envisaged). In this case, the models were trained for 100 epochs with 1344 iterations per epoch (i.e. a total of 134,400 iterations). Other values are possible and envisaged (such as e.g. 1088 iterations per epoch). The training was performed using a stochastic gradient descent with momentum=0.9, optimising at an initial learning rate of 0.05. The Factor for L2 regularization was set to 0.0001. The minimum batch size was set to 16 images and the training data was shuffled at every epoch. The training data is divided in mini-batches, where a mini-batch is a subset of the training set that is used to evaluate the gradient of the loss function and update the weights of the model. If the mini-batch size does not evenly divide the number of training samples, then the training discards the training data that does not fit into the final complete mini-batch of each epoch. Shuffling the training data between every epoch avoid the same data being thrown way at every epoch. A piecewise learning rate schedule was used, where the software updates the learning rate every certain number of epochs by multiplying with a given factor. The gradient threshold value was set to 0.05 (if the L2 norm of the gradient of a learnable parameter is larger than this value, then the gradient is scaled so that the L2 norm equals the gradient threshold). Other values are possible and envisaged for each of the above parameters. All of the parameters used for training (including but not limited to the number of epochs, iteration, stop criteria, learning rate, regularization factor, batch size, learning rate schedule, gradient threshold, etc.) may vary depending on the particular implementation and the skilled person would be able to identify suitable values as a matter of routine. The loss and percentage accuracy was monitored during learning to ensure that the model converged to a good solution. The training was performed using mini-batches and mini-batch accuracy was calculated for each fold at every iteration. Training took approximately 2-3 days for the most complex networks (7 classes, see below), although shorter training times could have been achieved with similar performance using a different stopping criterion. Indeed, in the case of the network training process illustrated on FIG. 8 (reaching a mini-batch accuracy of 85.8% at the final iteration), a min-batch accuracy of 93.0% was already reached at iteration 27620 (epoch 21). The accuracy remained above 70% for almost all iterations thereafter. The training was performed on a Linux cluster running on Centos 7, and three Tesla K80 GPU support.

Each of the training images was manually annotated by selecting and labelling areas of interest. Each pixel in a manually segmented area was then automatically assigned the corresponding ground truth class label. Areas that are not annotated (e.g. background/void areas) do not influence the training. In other words, the models were only penalized for failing to correctly identify labelled pixels or for wrongly identifying unlabeled pixels as belonging to one of the labelled classes. Results from trained models were independently checked by two clinicians who each reviewed 10-20 images comprising a combination of randomly selected images and "difficult" images (e.g. images showing uncommon morphologies). The results of this process were used to compare models, identify commonly misidentified tissue compartments, and identify configurations (e.g. sets of segmentation classes) that produce the best results.

The results of the final trained model (prediction from the trained network on all of the 84 images) were then manually evaluated again by a clinician, to ensure that the areas identified by the machine learning model were clinically relevant. During this final check, the clinician assigned a manual score to each image for each tissue compartment, which provides an evaluation of the metrics derived from the machine learning model (results on FIG. 12 and discussed below). In particular, for each sub-tissue compartment that was associated with a label in the training data, the volume of tissue in the compartment was calculated based on the output of the machine learning model. For each stack of images, the volume of a compartment is calculated by multiplying the area assigned to the compartment in each image by 50 μm, and summing these values across images in a stack. A clinician then reviewed the segmented image stack and evaluated, for each tissue compartment, whether the result from the machine learning model under or over-estimated the volume of tissue, and estimated a percentage associated with this error. For example, a clinician may identify that the volume of a particular tissue was underestimated by 10%. This can then be used to calculate a "clinician volume", which compared to the volume from the machine learning algorithm over the entire data set by calculating an intraclass correlation coefficient (ICC).

Definition of Classes and Annotation of Image Contents from Skin OCT Images

Figure 6A:
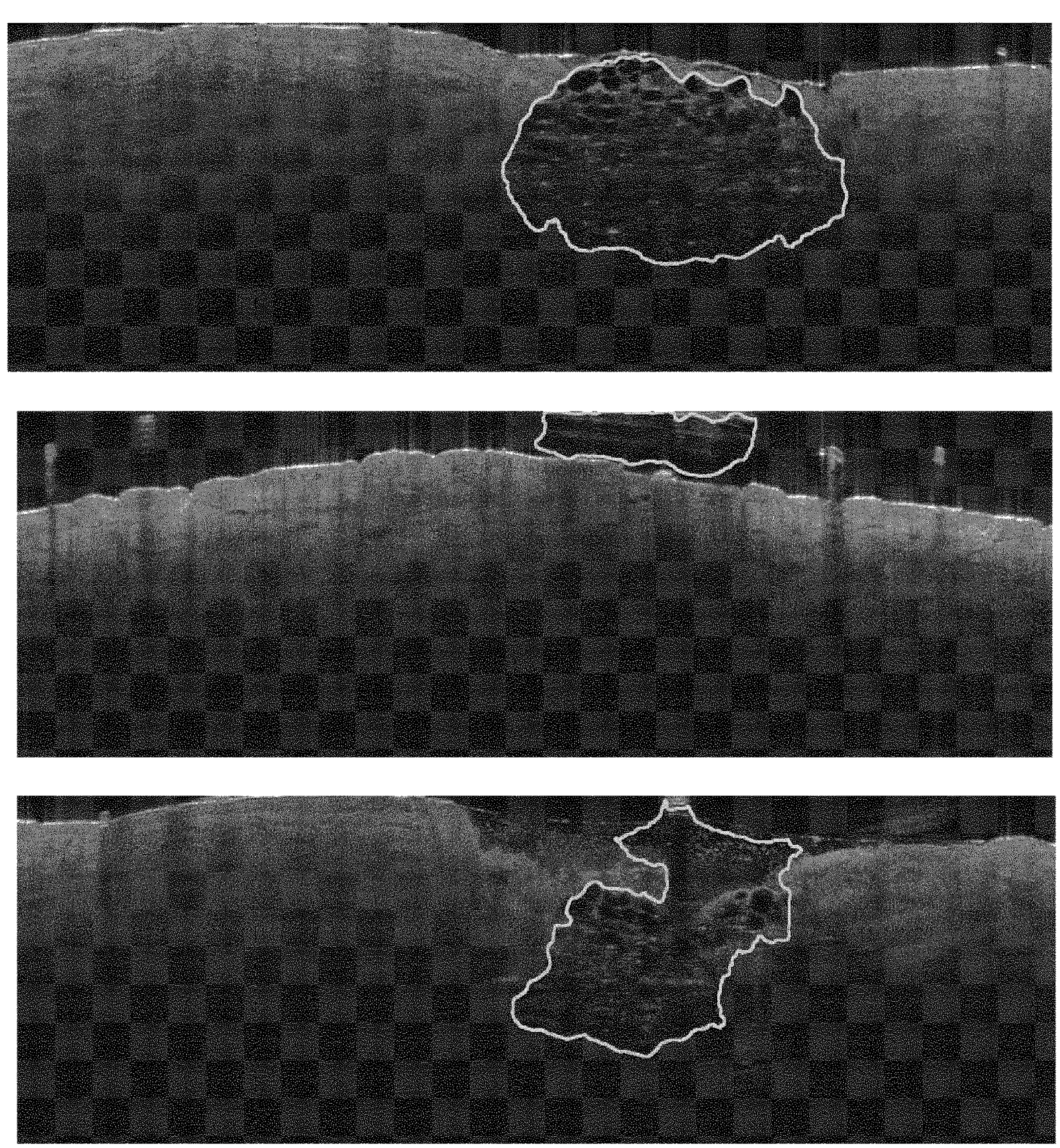
FIG. 6: 2D OCT images of wound segmented into two compartments. i) wound; ii) other (not wound). A. Segmentation results from a deep learning model trained using wound/not-wound labels. B. Examples of training data (top panel) and segmentation results (all other panels—overlaid onto original images in the two large middle panels, presented next to the corresponding original images in the smaller bottom panels where white=pixels identified as wound tissue) from a deep learning models trained using wound labels obtained by combining granulation tissue and collagen labels.

As mentioned above, at the outset of this work, no strict definition of what qualifies as "wound tissue" that is visible in OCT images was available. The assessment of which visible structures in an OCT image correspond to wound tissue was only done in research settings so far, and was performed manually based on subjective criteria, by trained clinicians with experience of looking at wounds and images thereof. No consistent definition of the morphology of wound tissue of even its various constituents was available. Thus, the present inventors set out to define differently textured regions within OCT images of wounds that could potentially be identified by machine learning. As a first step, a simple segmentation process based on two classes (wound, other) or three classes (wound, intact tissue, outside) was trialed. Examples of these are shown on FIG. 6A, where segmentation results for a deep learning model that only identifies wound tissue (wound vs other) are shown. As can be seen on FIG. 6A, although the model performed well for some cases (see top images) there were misclassified examples where external structures were erroneously identified as wound tissue (middle image) or where the wound tissue was incompletely segmented (bottom image).

The present inventors reasoned that these misclassifications occurred at least in part because wound tissue is not homogeneous in appearance. Thus, the deep learning model may have been unable to identify visual features that are common to all wound tissue but not present in other areas of the images. The inventors therefore considered the significance of tissue pathology of wound as well as the frequency of morphological appearances in typical skin OCT images, to identify a plurality of classes that could be associated with improved accuracy. They decided to define seven distinctive image sub-types within the OCT image of a skin wound, namely neoepidermis, clot, granular tissue, collagen, intact tissue, blood (liquid) and outside (also referred to as "void" or "background"). These compartments were chosen based on their significance to the pathology of the wound, as well as based on their distinctive morphology that could be identified by clinicians trained to look at OCT images of wounds and experts at looking at MRI images of wounds (on which many structures can be clearly seen). Indeed, the inventors found that within each single one of these image subtypes (tissue subcompartments) within and/or across patients, common image appearances and texture can be seen. By contrast, between image subtypes, differences in image appearances can be observed. For example, collagen tissue shows horizontal periodical image patterns with bright pixels as the fibroblast cells, granular tissue however shows clear honeycomb-like hexagon structure. These differences could be observed by clinicians, and hence the inventors postulated that a deep learning model may also be able to identify these compartments on the basis of the morphological differences visible in the images.

Thus, a final model trained on data labeled with ground truth labels for the above 7 classes was obtained. This was confirmed to have excellent accuracy by comparison with the ground truth labels and by independent assessment of the segmented images by a clinical expert.

Figure 6B:
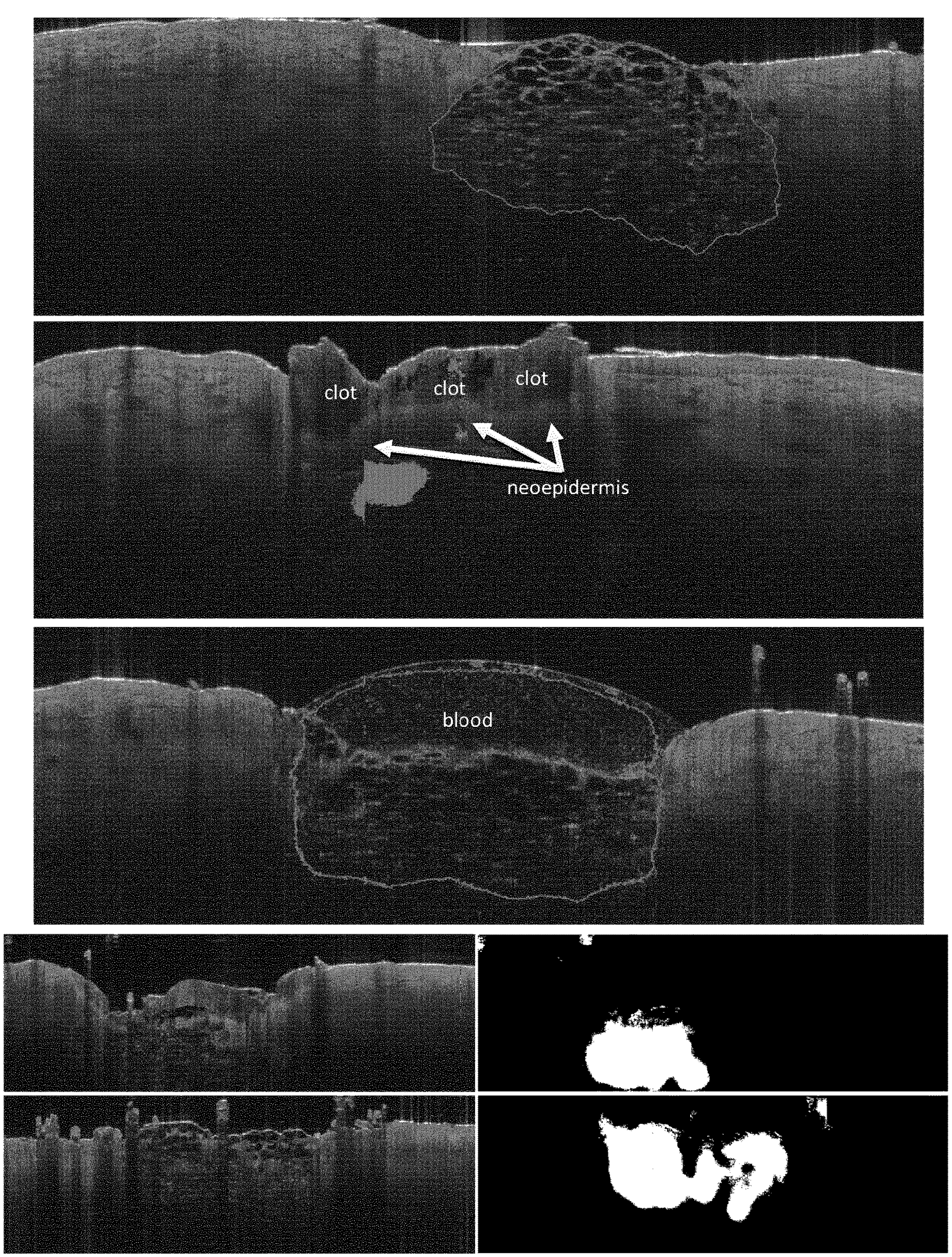

To further investigate the benefits of a model trained to separately identify a plurality of different types of wound tissue, the inventors used a subset of the labelled training images (10 images, each of 460×1324 pixels) to train a more simplistic model comprising only 2 classes, namely wound tissue and non-wound tissue. The ground truth labels for "wound tissue" were obtained by combining the areas in the fully labelled training data set labelled as granulation tissue and collagen. These two types of tissues formed the bulk of wound tissue in most images and together correspond to what is most easily identifiable as wound tissue to the untrained eye. Thus, this model was trained to recognize only two classes (wound/not wound), but with the advantage that what is labelled as wound is more homogeneous as than in the images of FIG. 6A as it only combines two different types of tissues (see example of training image with ground truth label, top panel of FIG. 6B). A good accuracy (mini-batch accuracy of 97.1% at the final iteration) was achieved during training of this model. Note that this accuracy is positively influenced by: (i) the use of ground truth labels that are derived only from two types of wound tissue and therefore provide relatively consistent information about what constitutes wound tissue, (ii) the overall accuracy being heavily influenced by pixels showing non-wound tissue (mostly intact tissue and background) being correctly classified as non-wound tissue (which represent the majority of the pixels in the images), (iii) the use of categories that capture much of the volume of wound tissue in most images such that misclassification of small areas of other types of tissues as either wound or not-wound has a comparatively small influence on accuracy, and (iv) the accuracy being calculated on a small subset selected from the 10 training images. Despite this good accuracy, close inspection of the results showed that clinically important areas of the images were misclassified, due to the use of a single combined "wound tissue" category. Exemplary results are shown in FIG. 6B. As can be seen in FIG. 6B, despite the overall good classification accuracy, areas of clot and neoepidermis were not detected as wound in some images (see second panel from the top), and areas of blood were wrongly classified as wound tissue (see third panel from the top). The two images and corresponding segmentation results at the bottom of FIG. 6B illustrate the points above, that good accuracy can be obtained due to the granulation tissue and collagen representing large areas of the wound and non-wound tissue (including background) being correctly identified as not wound, even though some areas are clearly mis-identified as wound. These results therefore show that training the classifier to identify a plurality of different types of wound tissues separately rather than as a combined wound category.

Post Processing of Segmentation Results

Further morphological image processing was then performed on the labelled images (segmentation mas) in order to show more meaningful continuous regions of sub-tissue components. In particular, a set of morphological operations was applied to each segmentation map to remove isolated pixels and small islands (assigning a class to all small islands of pixels that are either labelled as non-intact tissue or that are unlabeled, using a nearest neighbor tree approach), and to smooth boundaries between classes (using a Fourier descriptors-based method as known in the art). This process was automated for each image, such that each stack of 120 images can be processed automatically, resulting in a stack of 20 images with labelled regions for each of the annotated classes. Any other methods for smoothing segmentation maps may be used.

Post-processing is optional and unlikely to influence the majority of the clinically relevant metrics discussed herein. However, it advantageously results in images that are easier to visualize and interpret by the human eye.

Metrics for Wound Assessment Derived from Image Classification and Segmentation

Figure 7A:
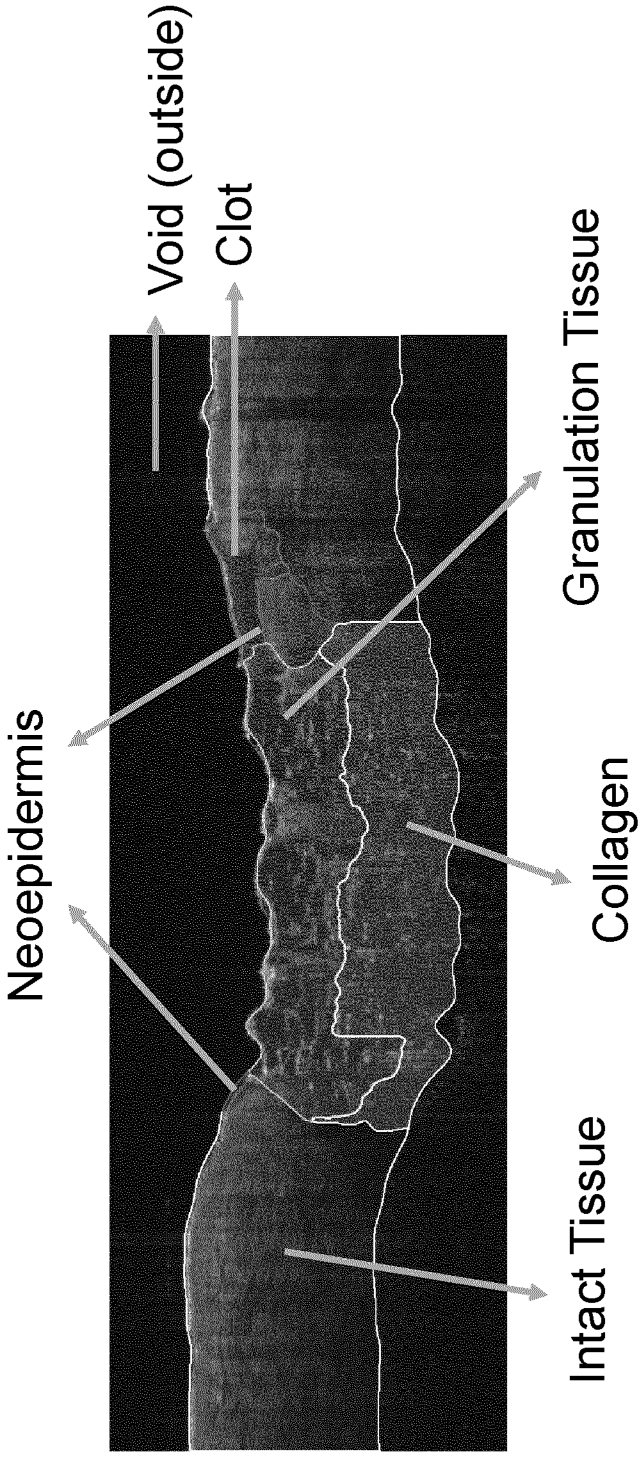
FIG. 7: A. 2D OCT image of wound segmented into compartments. i) void (outside/background); ii) intact tissue; iii) collagen; iv) granulation tissue (with sponginess morphology); v) neoepidermis; vi) clot & vii) blood (in liquid form). B. Raw 2D OCT image of wound (top panel), the raw segmentation map corresponding to the raw image (middle panel), and the corresponding 2D OCT image of wound segmented into compartments (bottom panel): intact tissue (I), wound collagen (C), granulation tissue (G), neoepidermis (N), clot (Ct), and blood (B). C. Raw 2D OCT image of wound (top panel), and the corresponding manual annotations for the training of the deep learning algorithm (bottom panel—the following manual annotations were provided: intact tissue (I), wound collagen (C), granulation tissue (G), neoepidermis (N), clot (Ct), and blood (B); outside/background areas were not annotated).
Figure 7B:
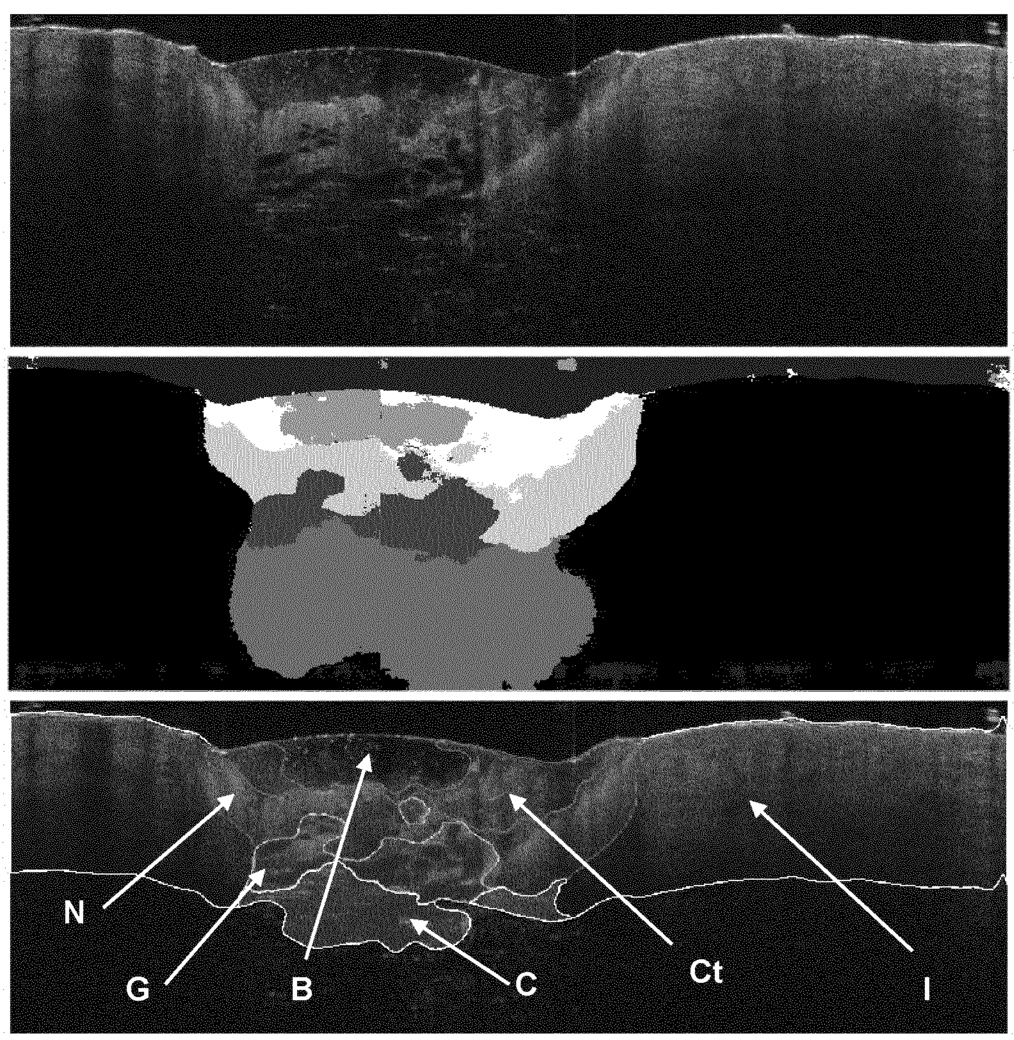
Figure 7C:
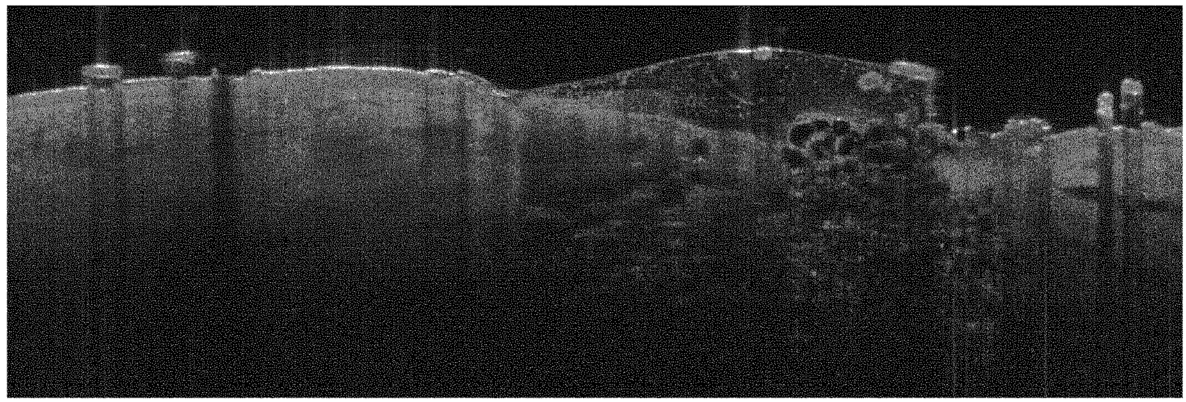
Figure 7C:
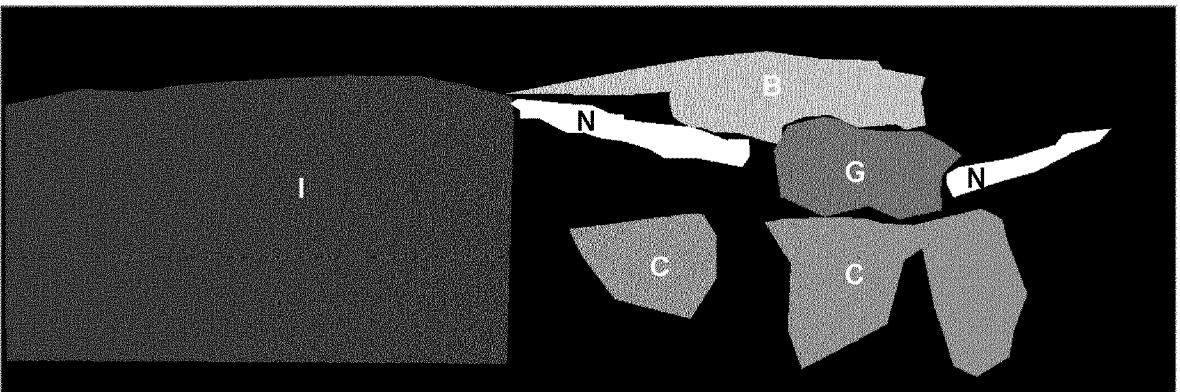

The final method described above takes a slice of scanned 2D OCT image (one colour channel) and performs the segmentation of an OCT image into 7 sub-tissue components, that exist in typical wound healing pathology, namely i) Outside (void) (also referred to as "background"); ii) Intact tissue; iii) Wound collagen; iv) Granular Tissue (also referred to herein as "sponge tissue" or "tissue with sponge morphology"; v) Neoepidermis; vi) Clot; and vii) Blood (in liquid form). An example analysis image depicting the areas listed (after post-processing) is provided as FIG. 7A. FIG. 7B shows another example, with the raw image at the top, the raw segmentation map in the middle, and the processed segmentation results at the bottom (overlaid on the image). FIG. 7C shows an example of the annotation data that was used to train the model that produced the results on FIGS. 7A-B, with the raw image at the top, and the manual annotations at the bottom. FIG. 7C shows that the annotation labels show relatively simplistic shapes (due to practical limitations of manual selection of areas), and only annotate compartments of relevance (e.g. the background is not highlighted). Nevertheless, extremely detailed and accurate segmentation results could be obtained as illustrated on FIGS. 7A-B. Further, the automated segmentation results, if accurate (which is the case for the present results) are likely to be more precise than what is practically feasible with manual annotation (even if clinician time was no object, which is not the case). This in turn means that metrics such as volumes derived from these segmentation results will also be more accurate.

Using the results of the segmentation (preferably after post-processing), the area ($mm^2$) of each sub-tissue components could be calculated in every image of a stack. In addition the volume ($mm^3$) of each sub-tissue components across 120 slices of tissues were also determined as described above, by multiplying the area in each slice by the thickness of the slice (here 50 μm). With knowledge of the volume, it was also possible to calculate the ratio of wound tissue within a 1 mm tissue depth. This is obtained by dividing the volume in a particular tissue compartment by the volume between the top of the image and a 1 mm penetration depth from the surface of the skin, excluding any volume labelled as "outside" and "blood (liquid)". The depth of 1 mm was chosen as a depth at which acceptable axial image resolution is still present. The surface of the skin was defined as the line formed using the top coordinates of any area labelled as any of the 7 categories other than "outside" and "blood (liquid)" (i.e. the highest 7 coordinate at any x location, that has been assigned a label that is any of: intact tissue, wound collagen, granular tissue, neoepidermis, and clot (see white top line on FIGS. 7A-B). The ratio of non-intact tissue within a 1 mm tissue depth could also be calculated using the sum of the volumes for the neoepidermis, granular tissue, clot and collagen. Additionally, it was possible to quantify the relative volumes of tissues in various compartments. For example, the ratio of the volume of granulation tissue to neoepidermis, and the ratio of the volume of granulation tissue to the sum of the volume of neoepidermis and clot. Further, the sum of volumes of tissue in multiple compartments could also be calculated, such as the total volume of non-intact tissue (sum of volumes of neoepidermis, granular tissue, clot and collagen), the sum of neoepidermis and clot tissue, etc, as well as the ratios of these sums to the volume of tissue within a 1 mm tissue depth. Finally, a value for the wound width could be determined on the basis of the segmentation result by considering the maximum width of all the non-intact tissue (including neoepidermis, collagen granulation tissue and clots). This could be obtained by determining wound width in every image of a stack, and selecting the largest wound width thus identified. Alternative approaches could be used such as e.g. selecting the top $x^{th}$ percentile of the wound width distribution thus determined. For example, the 90th, 95th 98th or 99th percentile could be used. The wound width metric was obtained primarily for comparison with the commonly used clinical metric obtained by measurement with a caliper, and the experimental clinical metric obtained by manual evaluation of OCT images. While the machine-learning derived wound width metric is more accurate than both manual metrics, these one dimensional metrics still provide considerably less reliable and less informative insights than more complex metrics such as volumes and metrics derived therefrom, which are newly available as a result of the methods described herein.

Amongst there, the volume of neoepidermis, clot tissue and granulation tissue (and the corresponding volume % as well as derived metrics such as ratios of these volumes) were investigated as key metrics of clinical relevance as these tissues are known to play a key role in the wound healing process. Indeed, increasing amounts of neoepidermis and clot are indications that the wound healing is progressing. The volume of collagen and intact tissue were also calculated but are not believed to be as clinically relevant. However, a deep learning model that also segments these compartments (as well as the outside compartment) was found to have better performance in identifying the compartments of major clinical relevance (neoepidermis, clot, granular tissue). This is because each of these classes have a distinct appearance and training the network to differentiate between these appearances improve the network's ability to identify the hallmark visual features of each class. Other metrics that were evaluated included the volume of non-intact tissue, the % non-intact tissue volume, the ratio of volumes of granulation tissue and neoepidermis, the combined volume of neoepidermis and clot, the % collagen volume, the % combined neoepidermis and clot volume, and the ratio of volumes of granulation tissue and combined neoepidermis and clot volume. In principle, any volume, % volume (relative to total volume within a certain depth from the skin surface, such as 1 mm, which can be obtained as explained above) or ratio of individual or combined compartments volumes can be obtained according to the methods described herein.

Results

Figure 8:
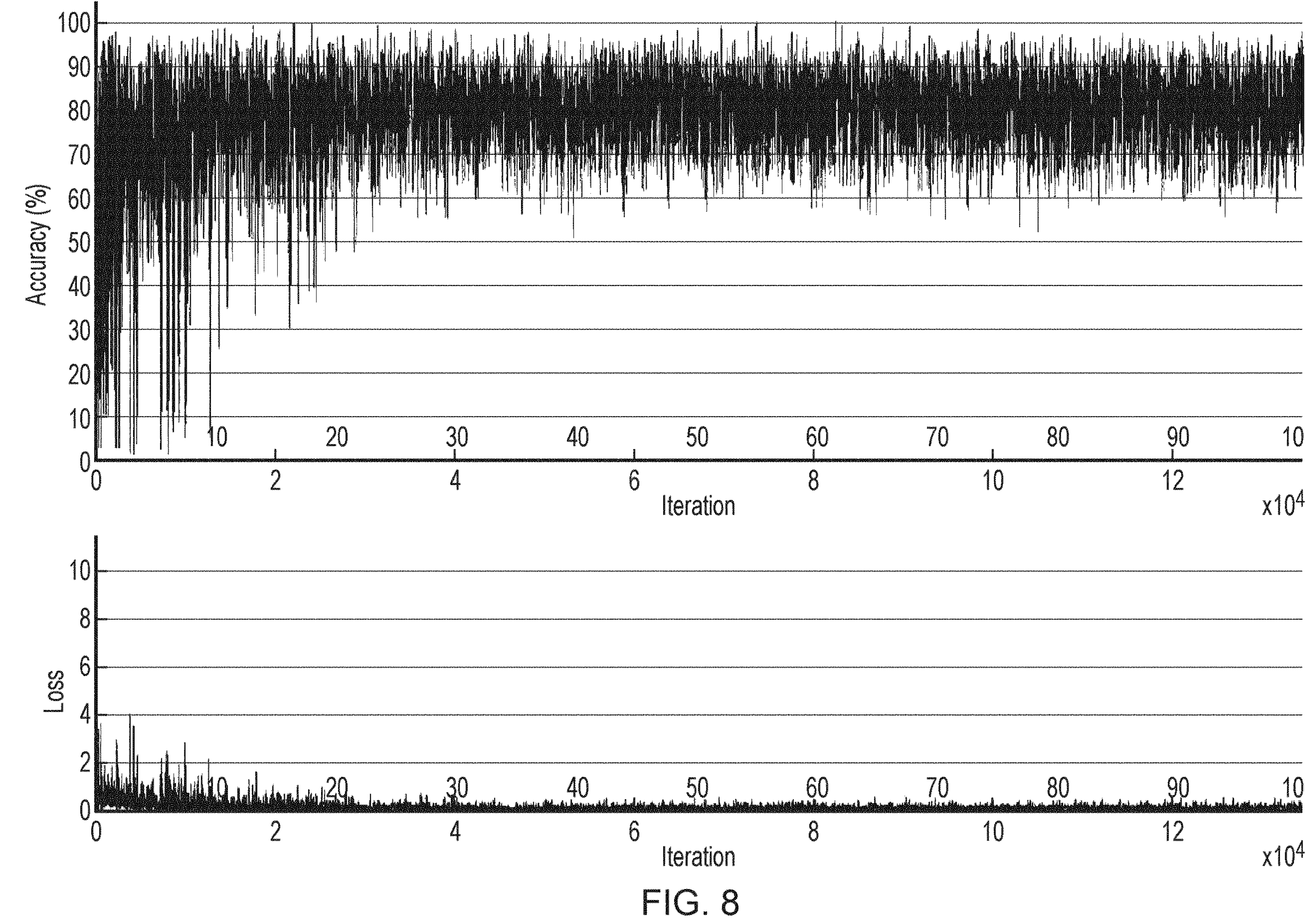
FIG. 8: Example of the percentage accuracy and loss (min-batch) during training of a deep learning model as described herein.
Figure 9:
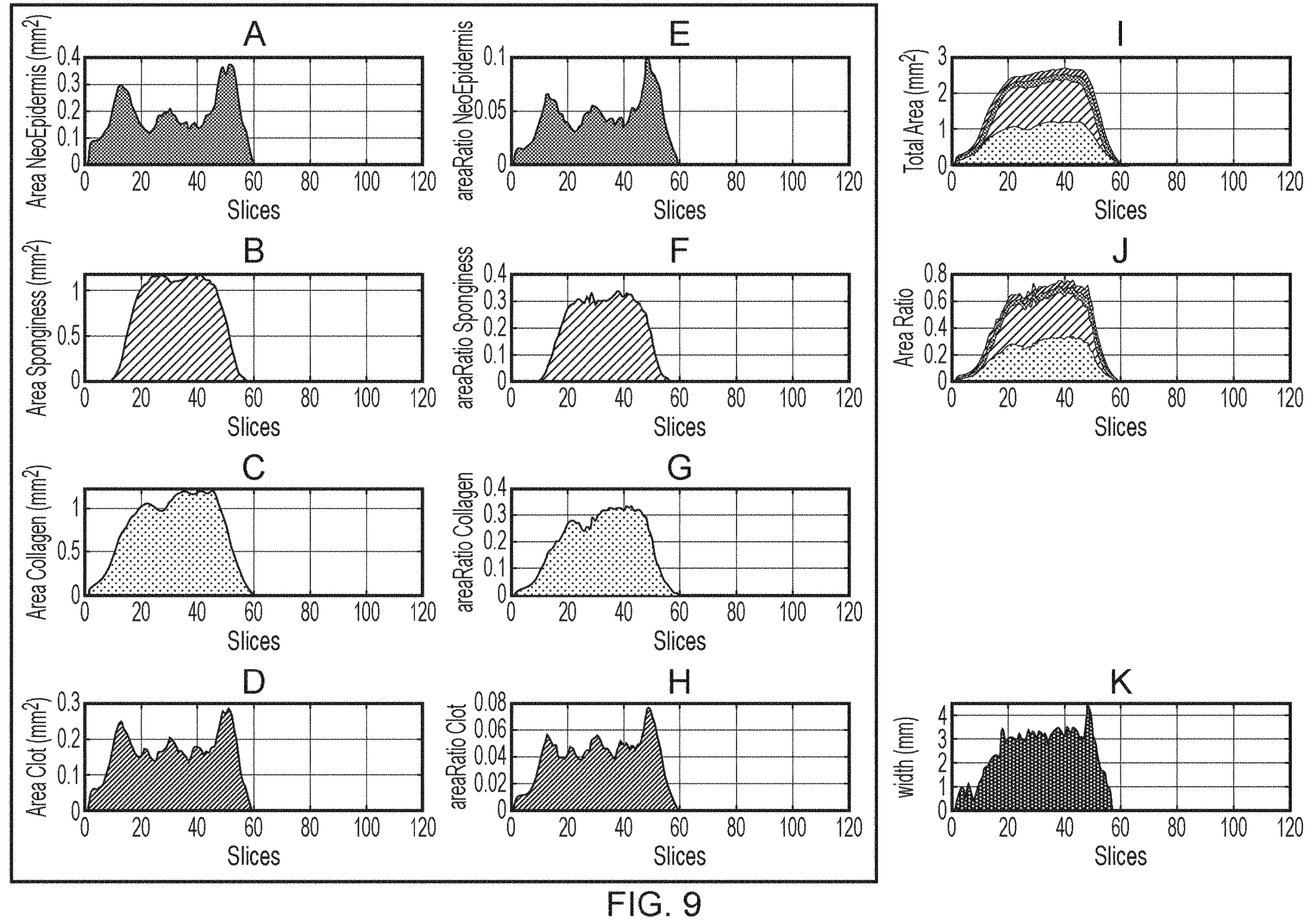
FIG. 9: Results of quantification of analysis of a stack of 2D OCT images of a wound by segmentation into compartments using machine learning and quantification of metrics derived therefrom. A-D. Area of each image in a stack of OCT images identified as neoepidermis (A), granulation tissue (B), collagen (C) and clot (D). E-H % area (relative to total tissue up to 1 mm depth) of each image in a stack of OCT images identified as neoepidermis (E), granulation tissue (F), collagen (G) and clot (H). I. Overlay of plots A-D. J. Overlay of plots E-H. K. Wound width determined in each image in a stack of OCT images based on the segmentation results (wound width is the maximum width of non-intact tissue, non-blood area identified in each slide, with the final wound width for a stack of images being the maximum width identified from the whole stack of images).
Figure 10:
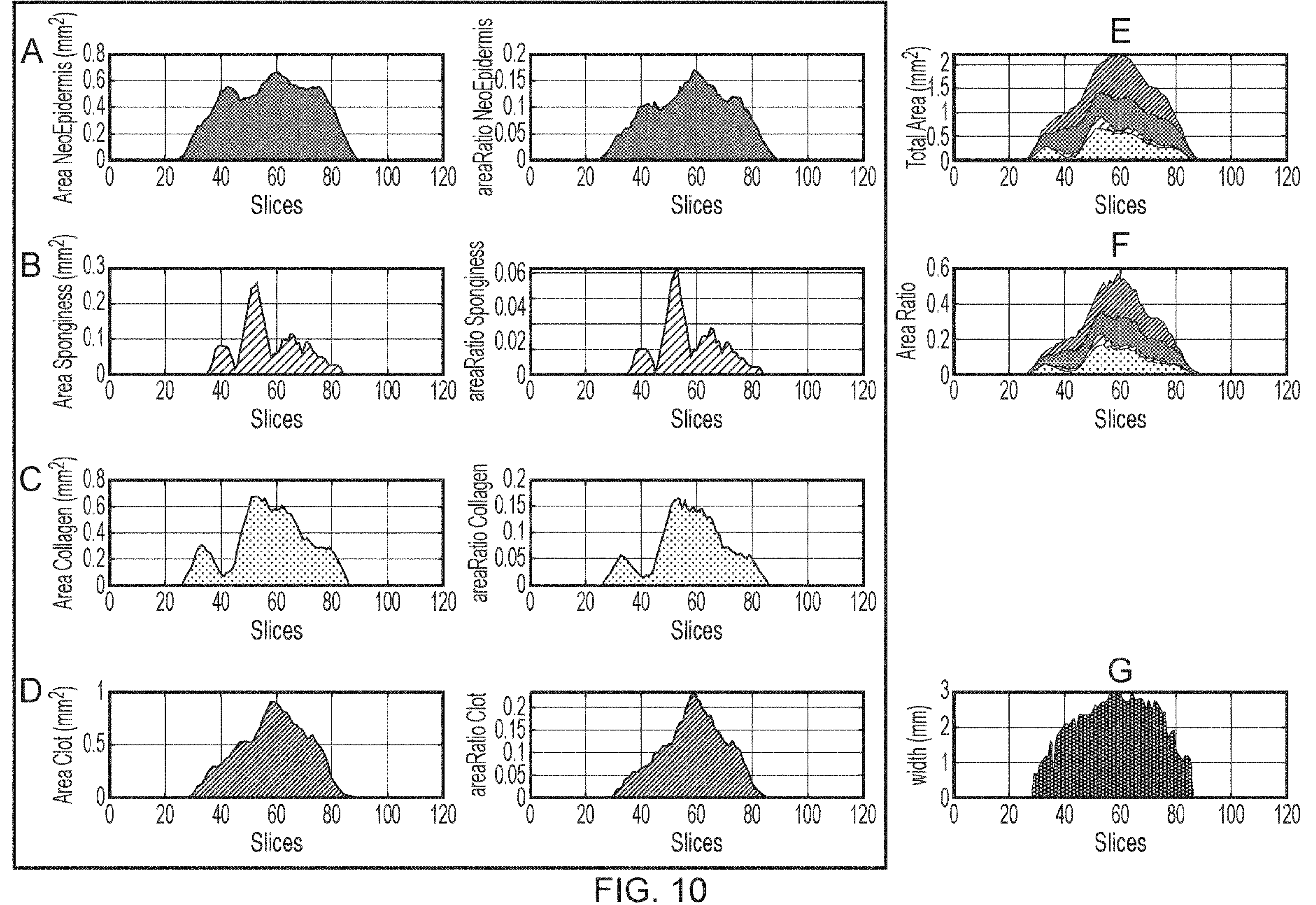
FIG. 10: Results of quantification of analysis of a stack of 2D OCT images of a wound by segmentation into compartments using machine learning and quantification of metrics derived therefrom. A-D. Area of each image in a stack of OCT images identified as neoepidermis (A), granulation tissue (B), collagen (C) and clot (D). E-H % area (relative to total tissue up to 1 mm depth) of each image in a stack of OCT images identified as neoepidermis (E), granulation tissue (F), collagen (G) and clot (H). I. Overlay of plots A-D. J. Overlay of plots E-H. K. Wound width determined in each image in a stack of OCT images based on the segmentation results (wound width is the largest dimension of non-intact tissue, non-blood area identified in an image).

Using the 7 classes described above (i.e. neoepidermis, clot, granular tissue, collagen, intact tissue, blood (liquid) and outside (void)), a deep learning model with a mini-batch classification accuracy of at the final iteration of the training could be trained. FIG. 8 shows an example of the percentage accuracy and loss during training of a u-net as described herein. FIGS. 9-10 show examples of the areas of tissue identified as neoepidermis (A), granulation tissue (B), collagen (C) and clot (D) in 2 stacks of OCT images of wounds obtained from 2 different patients. The corresponding volumes of tissue within 1 mm depth are also shown (E-H). These figures also show the area curves (I) and volume curves (J) for each of these compartments overlaid on top of each other. Finally, these figures also show the estimated wound width in mm (K). As can be seen by comparing plots A-J across FIGS. 9-10, different samples are associated with vastly different profiles of the tissues in the different compartments identified. Thus, this data demonstrates that the methods described herein could capture differences between patients, and hence could be used to monitor the wound healing process. In the particular context of a clinical trial, this indicates that the method would be useful in identifying any impacts of treatment group, time to treatment, etc. on the wound healing process. Additionally, looking at plots K in both figures shows that the wound width can vary significantly along the 120 images of a stack. Thus, even if manual identification of the wound width was based on objective criteria and had very good accuracy and reproducibility within a single image, the choice of which image to use for the measurement (which is arbitrary and in practice cannot result from a thorough investigation or comparison of all images of a stack) would likely still result in significant variability and loss of accuracy. Thus, these results show that the present methods have the potential to improve the accuracy and reliability of detection of metrics that are currently manually determined in research settings. Further, due to the automated, fast and reliable nature of the process, the present methods also make it realistic to use these metrics in clinical practice rather than being limited to research settings.

Figure 11:
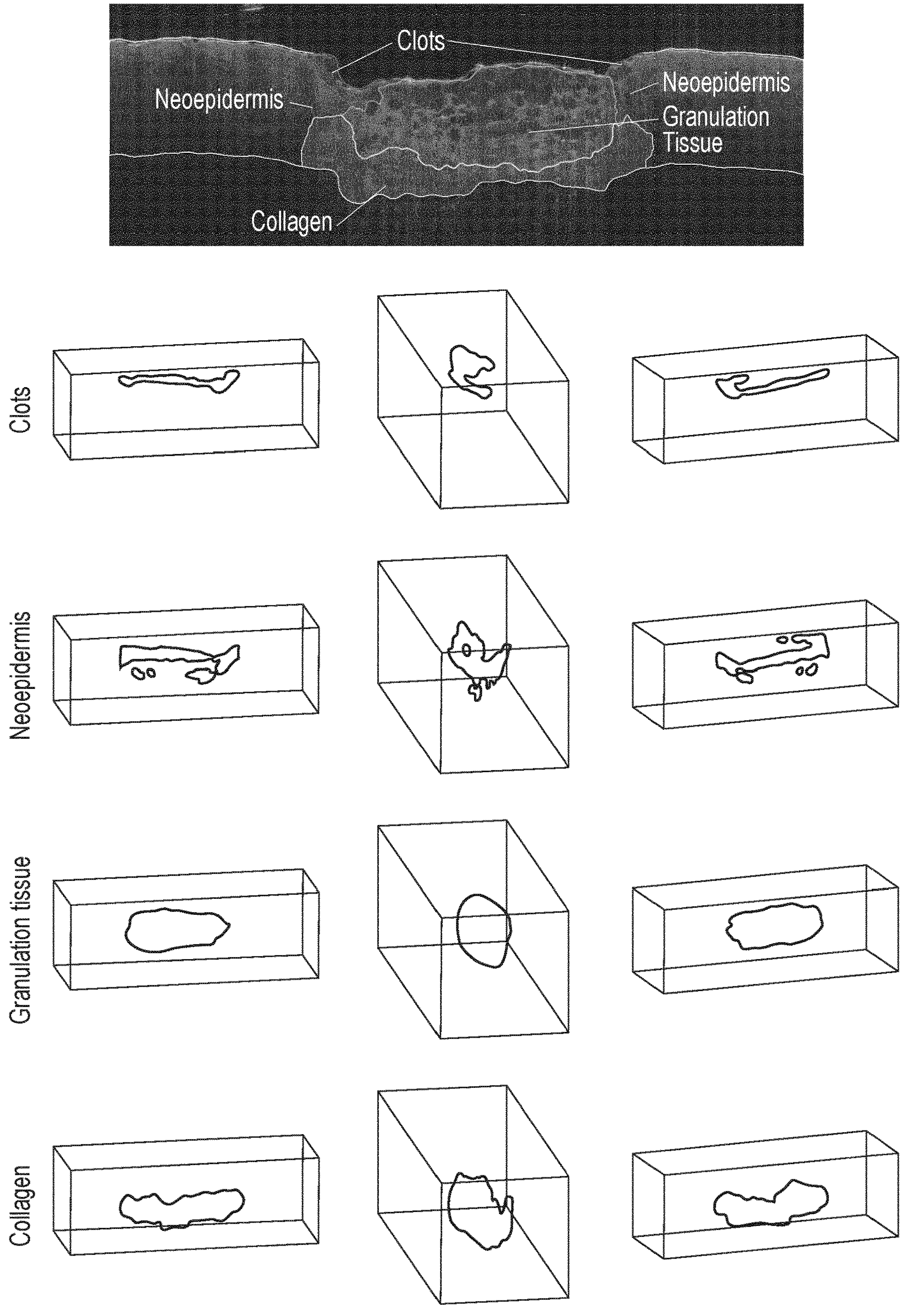
FIG. 11: Results of segmentation of a stack of 2D OCT images of a wound using machine learning. The top plot shows a single 2D OCT image selected from the stack, with the neoepidermis, collagen, clot and granular tissue compartments indicated in the overlaid segmentation map. The segmentation map was obtained using a 7 classes segmentation process as used in FIGS. 7-11. The plots in each of the subplots show the 3D segmentation maps for the clot, neoepidermis, granular tissue and collagen compartments (obtained by combining the outputs of the analysis of each of the individual 2D images forming the complete stack), each visualized from 3 different angles.

FIG. 11 shows an example of the result of analysis of a stack of OCT images of a wound using a deep learning model as described herein. The figure illustrates that 3D segmentation maps may advantageously be reconstructed from the results obtained from single images, and these can be visualized in 3 dimensions. This may enable to get a more in depth understanding of the morphology of a wound, and how this changes during the healing process. Such an understanding simply could not be obtained using the methods of the prior art at least because (i) there was no method to collectively analyse all of the images of a stack, and (ii) there was a lack of understanding of the physiological meaning of any visual information that is present in OCT images of wounds.

Figure 12:
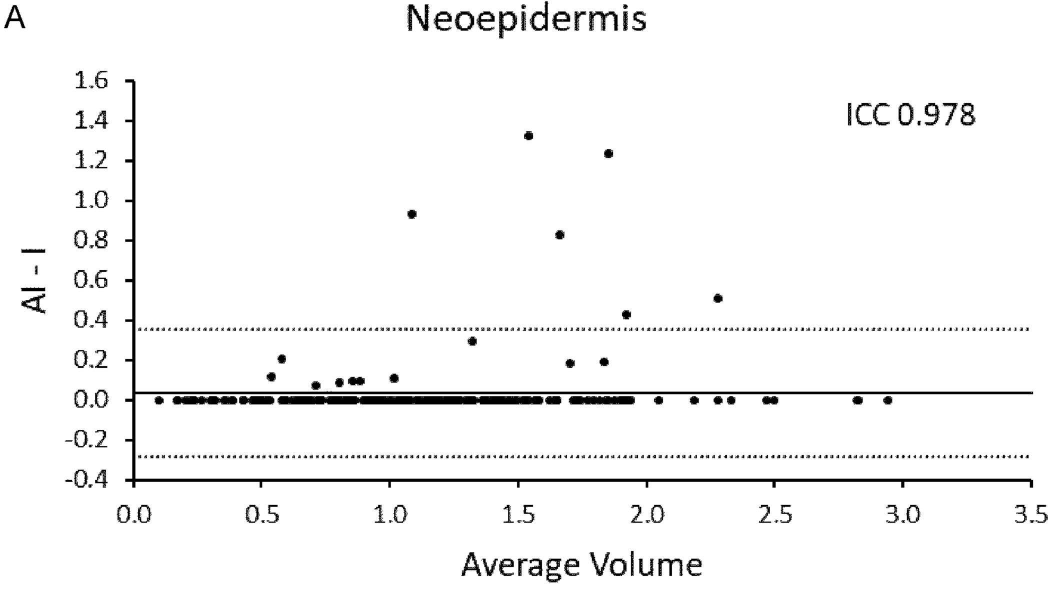
FIG. 12: Bland-Altman plot showing a comparison between the volume of tissue labelled in each of the neoepidermis (A), granulation tissue (B), collagen (C) and clot (D) by trained experts and by a machine learning algorithm trained to identify 7 compartments in OCT images of wounds (intact tissue, void, neoepidermis, blood, clot, granulation tissue, collagen). 204 samples for 28 patients at different stages of a clinical trial were compared in this study. For each point, the x-axis value is the volume for the respective comportment obtained from the machine learning results (A: neoepidermis, B: granulation tissue, C: collagen; D: clot), and the y-axis indicates the corresponding differences in comparison with the volume manually estimated by a clinician. Each plot also indicates the value of the ICC (intra-class correlation coefficient), which indicates the extent of the agreement between machine learning algorithm and a clinician in the quantification of a tissue compartment. ICC values close to 1 indicates high agreement degree of agreement between a clinician and the machine learning algorithm.
Figure 12:
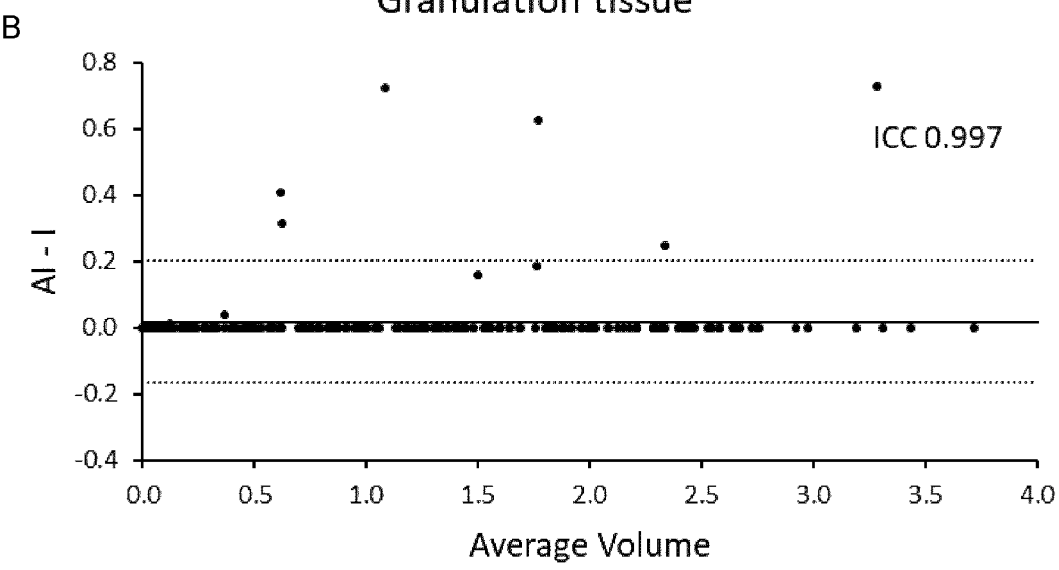
Figure 12:
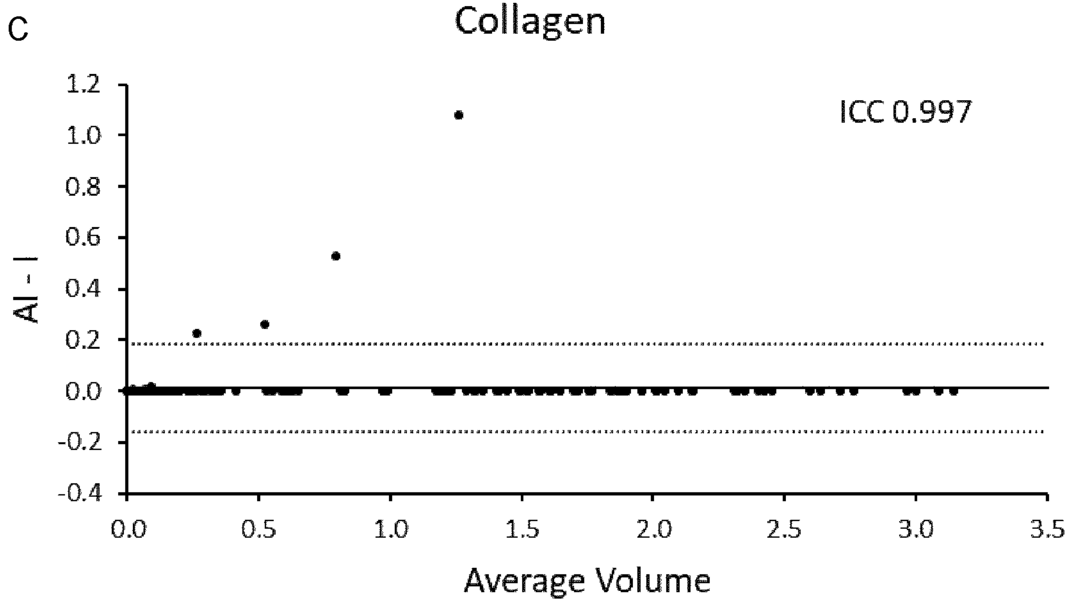
Figure 12:
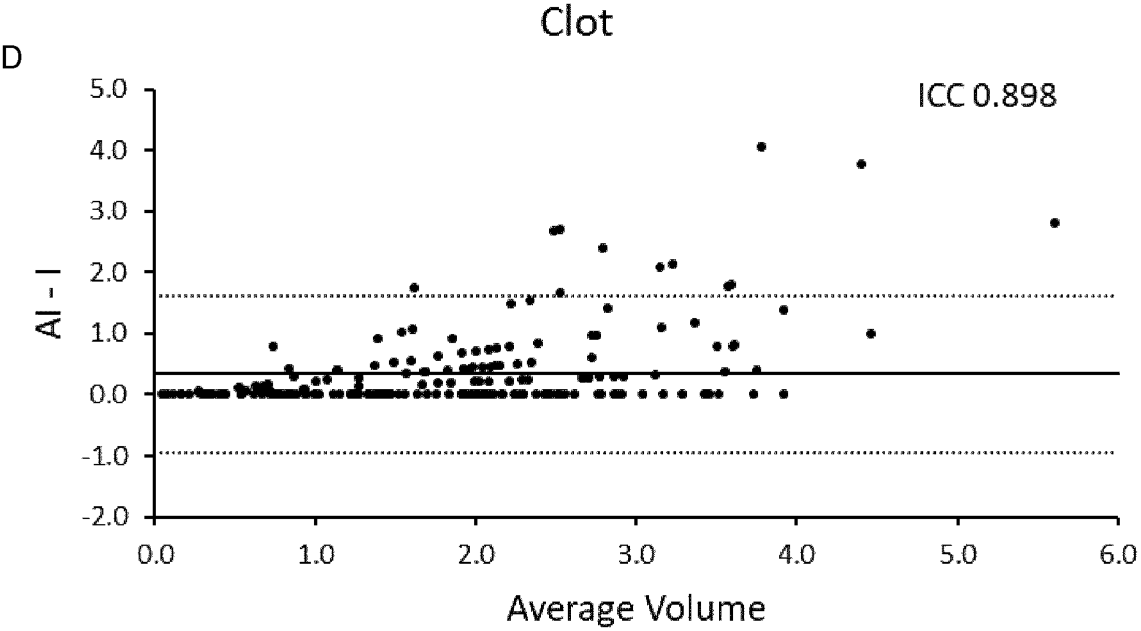
Figure 13:
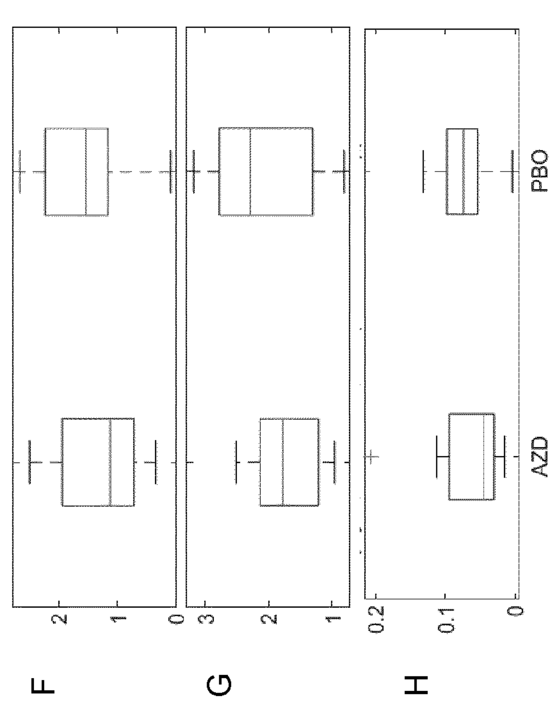
FIG. 13: Comparison between various metrics of wound healing derived from automated analysis of stacks of 2D OCT images of wounds from patients treated with AZD4017 (AZD) and placebo (PBO), two days after wounding and after 2 days of treatment (i.e. wounding at day 0 of treatment). A. Volume of tissue identified as neoepidermis (p=0.973). B. Volume of tissue identified as clot (p=0.868). C. Ratio of the volume of tissue identified as neoepidermis to the volume of tissue within 1 mm of the skin surface (p=0.976). D. Ratio of the volume of tissue identified as clot tissue to the volume of tissue within 1 mm of the skin surface (p=0.778). E. Wound width (p=0.405) (equivalent to the results shown on FIG. 4, top plot, obtained by manual inspection). F. Volume of tissue identified as granulation tissue (p=0.456). G. Volume of tissue identified as collagen (p=0.116). H. Ratio of the volume of granulation tissue to the volume of tissue within 1 mm of the skin surface (p=0.670). All p-values are from a standard t-test.
Figure 13:
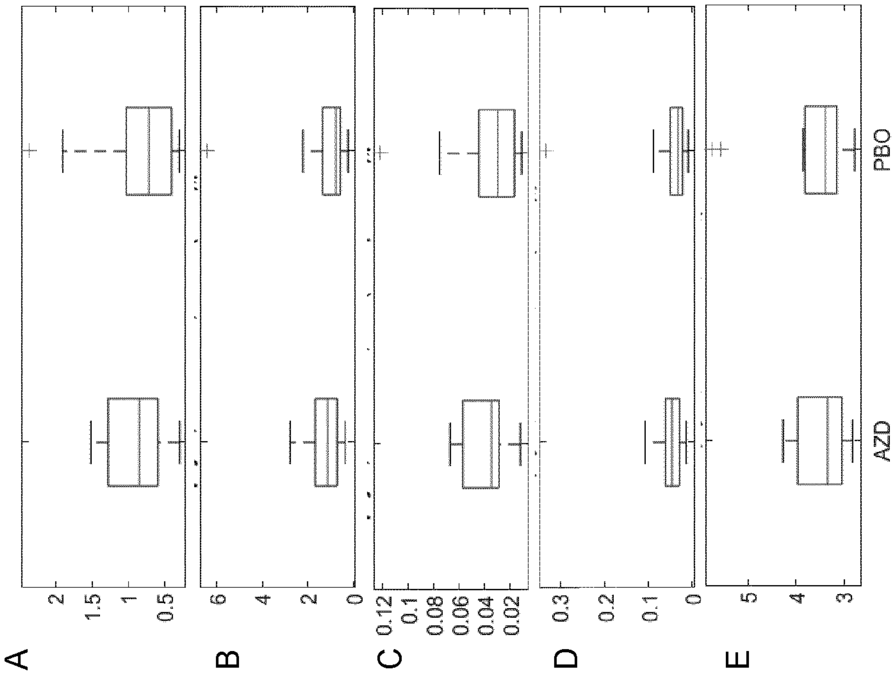
Figure 14:
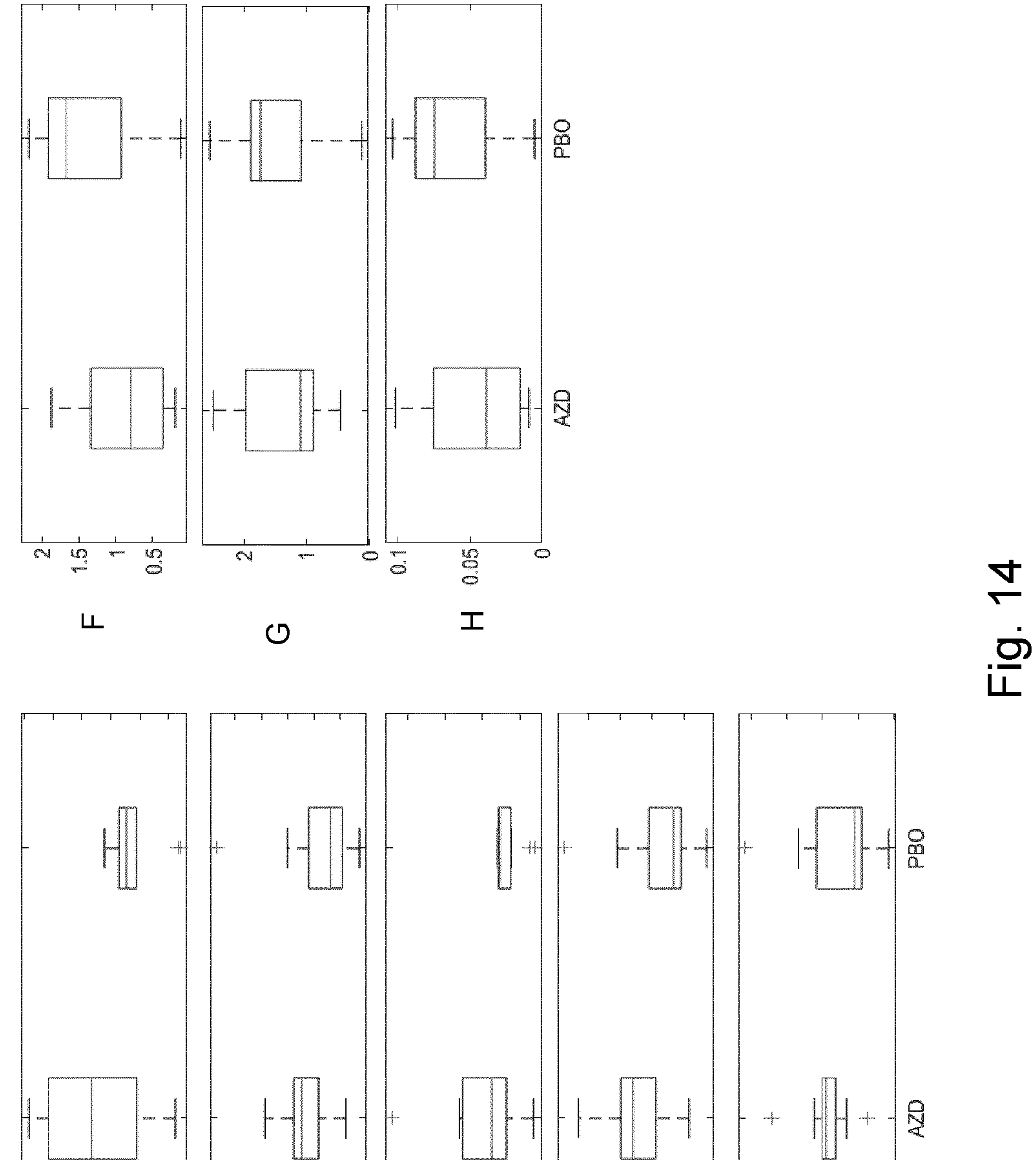
FIG. 14: Comparison between various metrics of wound healing derived from automated analysis of stacks of 2D OCT images of wounds from patients treated with AZD4017 (AZD) and placebo (PBO), two days after wounding and after 30 days of treatment (i.e. wounding at day 28 of treatment). A. Volume of tissue identified as neoepidermis (p=0.0214). B. Volume of tissue identified as clot (p=0.243). C. Ratio of the volume of tissue identified as neoepidermis to the volume of tissue within 1 mm of the skin surface (p=0.0399). D. Ratio of the volume of tissue identified as clot tissue to the volume of tissue within 1 mm of the skin surface (p=0.112). E. Wound width (p=0.412) (equivalent to the results shown on FIG. 4, bottom plot, obtained by manual inspection). F. Volume of tissue identified as granulation tissue (p=0.0796). G. Volume of tissue identified as non-intact tissue (i.e. sum of volumes of tissues identified as neoepidermis, clot, granulation tissue and collagen) (p=0.725). G. Volume of tissue identified as collagen (p=0.463). L. Volume of tissue identified as neoepidermis or clot (p=0.0701). H. Ratio of the volume of granulation tissue to the volume of tissue within 1 mm of the skin surface (p=0.186). All p-values are from a standard t-test.
Figure 15:
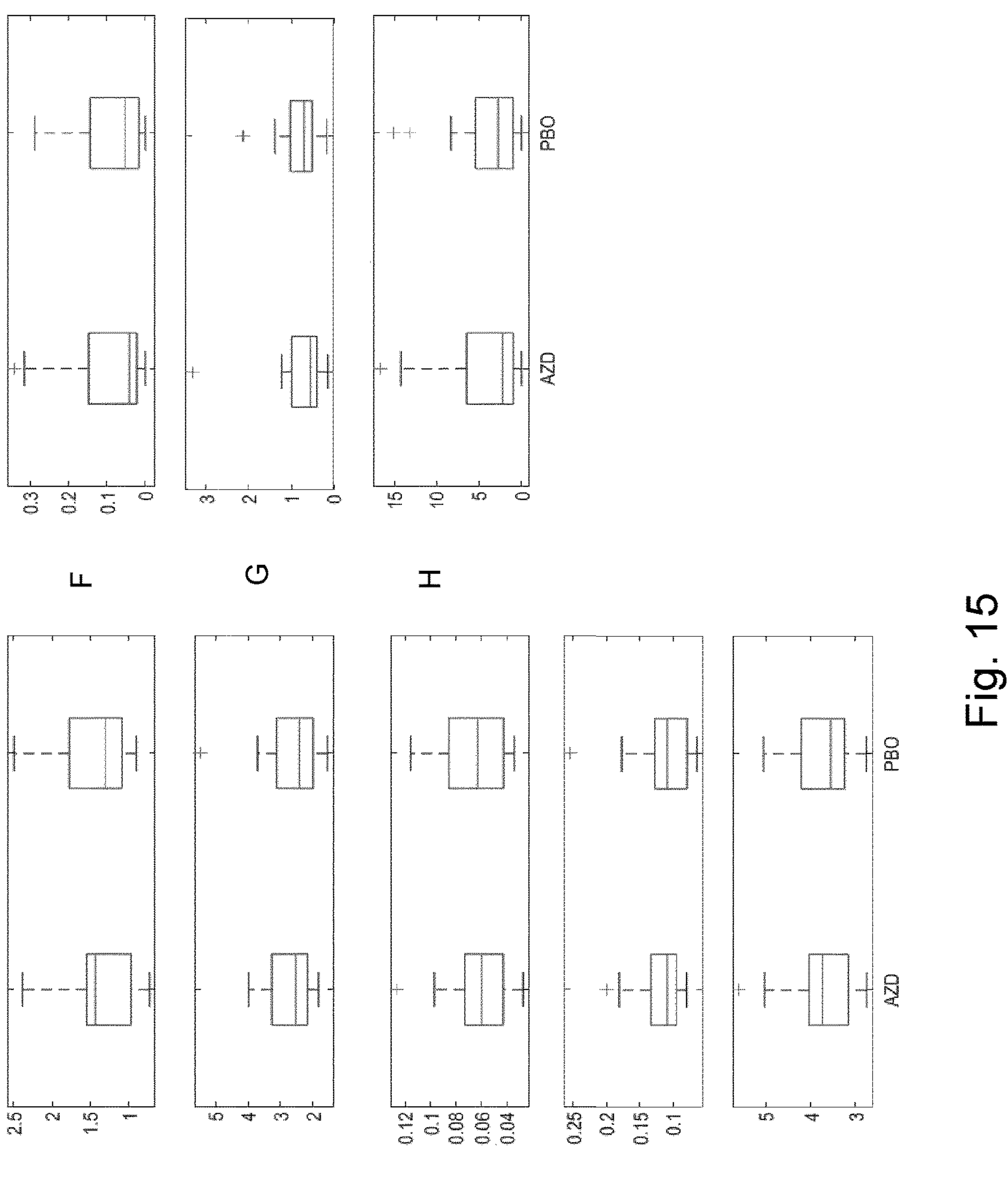
FIG. 15: Comparison between various metrics of wound healing derived from automated analysis of stacks of 2D OCT images of wounds from patients treated with AZD4017 (AZD) and placebo (PBO), 7 days after wounding and after 7 days of treatment (i.e. wounding at day 0 of treatment). A. Volume of tissue identified as neoepidermis (p=0.651). B. Volume of tissue identified as clot (p=0.898). C. Ratio of the volume of tissue identified as neoepidermis to the volume of tissue within 1 mm of the skin surface (p=0.725). D. Ratio of the volume of tissue identified as clot tissue to the volume of tissue within 1 mm of the skin surface (p=0.879). E. Wound width (p=0.779). F. Volume of tissue identified as granulation tissue (p=0.906). G. Volume of tissue identified as collagen (p=0.811). L. Volume of tissue identified as neoepidermis or clot (p=0.930). H. Ratio of the volume of granulation tissue to the volume of tissue within 1 mm of the skin surface (p=0.953). I. Ratio of the volume of tissue identified as non-intact tissue to the volume of tissue within 1 mm of the skin surface (p=0.899). J. Ratio of the volume of tissue identified as granulation tissue to the volume of tissue identified as neoepidermis (p=0.877). All p-values are from a standard t-test.
Figure 16:
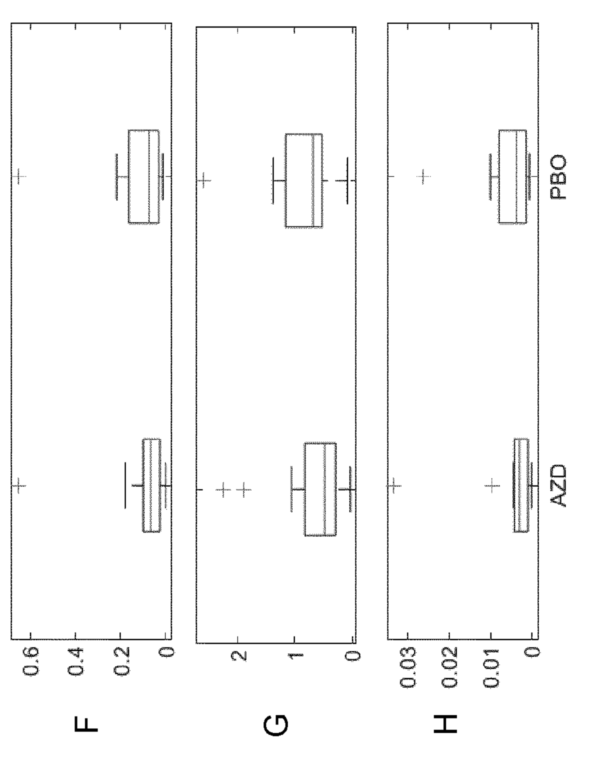
FIG. 16: Comparison between various metrics of wound healing derived from automated analysis of stacks of 2D OCT images of wounds from patients treated with AZD4017 (AZD) and placebo (PBO), 7 days after wounding and after 35 days of treatment (i.e. wounding at day 28 of treatment). A. Volume of tissue identified as neoepidermis (p=0.615). B. Volume of tissue identified as clot (p=0.131). C. Ratio of the volume of tissue identified as neoepidermis to the volume of tissue within 1 mm of the skin surface (p=0.462). D. Ratio of the volume of tissue identified as clot tissue to the volume of tissue within 1 mm of the skin surface (p=0.108). E. Wound width (p=0.638). F. Volume of tissue identified as granulation tissue (p=0.782049). G. Volume of tissue identified as collagen (p=0.471). L. Volume of tissue identified as neoepidermis or clot (p=0.203). H. Ratio of the volume of granulation tissue to the volume of tissue within 1 mm of the skin surface (p=0.958). I. Ratio of the volume of tissue identified as non-intact tissue to the volume of tissue within 1 mm of the skin surface (p=0.407). J. Ratio of the volume of tissue identified as granulation tissue to the volume of tissue identified as neoepidermis (p=0.903). All p-values are from a standard t-test.
Figure 16:
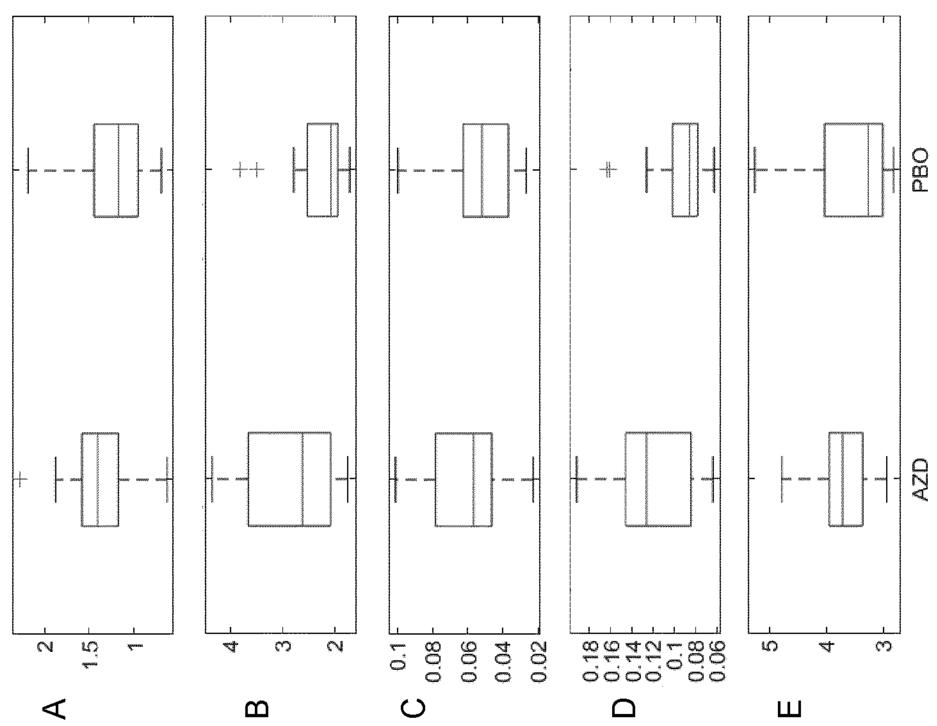

FIG. 12 compares the results of the analysis of stacks of OCT images of wounds using a deep learning model as described herein, and the corresponding metrics derived from manually provided labels for the same images, for 204 samples from 28 patients (as explained above). As can be seen on these plots, the predictions from the methods described herein were in excellent agreement with the assessments by clinicians for all clinically relevant wound tissue compartments (including neoepidermis, granulation tissue, collagen and clot). Indeed, the intra-class correlation values are close to 1 for all tissues (indicating a high agreement in the quantification of a tissue compartment between the machine learning results and a clinician) and the majority of values in the Bland-Altman plots (which show, for each sample, the difference between the machine learning-based values and the corresponding clinician assessment, as a function of the average of these two values) are close to 0 (0 indicating a perfect agreement). Comparing FIGS. 12A-C and 12D, it can be observed that the ICC is lower for the clot tissue compartment than for the neoepidermis, collagen and granulation tissue compartments (which remaining excellent). This suggests that the clot tissue has a more challenging morphology to classify (potentially more diverse) than the other three types of tissue analysed. Increasing the amount of training data would likely improve this situation.

FIGS. 13-16 demonstrate the use of the results of the analysis of stacks of OCT images of wounds using a deep learning model as described herein to derive metrics of clinical significance to compare patients in a treated vs placebo group in a clinical trial. For example, the comparison between AZD4017 (14 patients) and placebo (14 patients) treated cases indicate that in the images obtained of the wounds on day 30, that is 2 days after wounding at day 28 of the study (i.e. after 30 days treatment with AZD4017 or placebo treatment) (FIG. 14), a statistically significant difference ($p<0.05$) between placebo and AZD4017 treatment in the extent of neoepidermis (i.e. new skin growth into wound site) can be observed (FIG. 14A). Other metrics reaching statistical significance when comparing these two groups of patients included the ratio of neoepidermis volume to total volume (as shown on FIG. 14C), the ratio of the volume of granulation tissue to neoepidermis (not shown, $p=0.0436$, t-test), and the ratio of the volume of neoepidermis and clot to total volume (not shown, $p=0.0397$, t-test). Other metrics such as the ratio of total wound volume [i.e. non-intact tissue (neoepidermis+sponginess+collagen+clot)], wound width, clot volume, clot volume ratio, etc. did not show a statistical significant improvement for the treatment (AZD4017) arm relative to placebo arm. However, this is likely due to the small size of the trial for at least some of these metrics (such as e.g. granulation tissue volume (shown on FIG. 14F) and clot tissue volume (shown on FIG. 14B) and corresponding ratios (shown on FIGS. 14H, 14D), which almost reach significance). Note that any metric that does not reach significance in these comparisons is not necessarily uninformative, and instead any such metric could be relevant in other clinically relevant situations. Further, by comparing the results at different time points following wounding and start of treatment (as shown on FIGS. 13-16), it was possible to identify which schedules of treatment and assessment are best suited to evaluated the effect of the drug. For example, comparing the morphology of the wounds after a short amount of time has elapsed may fail to notice important differences between groups. Thus, the methods described herein were able to confirm the positive effects of AZD4017 treatment following the wound challenge, by rigorously showing an increase in neoepidermis (i.e. skin growth into the wound site) and indicating a likely increase in the extent of blood clotting and formation of granulation tissue in the wound. The methods described herein were further able to provide richer information about the wound healing process in the presence or absence of the drug.

REFERENCES

Sen C K, Gordillo G M, Roy S, Kirsner R, Lambert L, Hunt T K, Gottrup F, Gurtner G C, Longaker M T. Human skin wounds: a major and snowballing threat to public health and the economy. Wound Repair Regen. 2009 November-December; 17(6):763-71. doi: 10.1111/j.1524-475X.2009.00543.x.

Nicholas S. Greaves MBChB Syed A. Iqbal PhD Tom Hodgkinson PhD Julie Morris MSc Brian Benatar FRC- Path Teresa Alonso-Rasgado PhD Mohamed Baguneid MD Ardeshir Bayat MBBS, PhD. Skin substitute-assisted repair shows reduced dermal fibrosis in acute human wounds validated simultaneously by histology and optical coherence tomography. *Br J Dermatol,* 2015. 23(4): p. 483-94. https://doi.org/10.1111/wrr.12308

N. S. Greaves B. Benatar S. Whiteside T. Alonso-Rasgado M. Baguneid A. Bayat. Optical coherence tomography: a reliable alternative to invasive histological assessment of acute wound healing in human skin? *Br J Dermatol,* 2014. 170(4): p. 840-50. https://doi.org/10.1111/bjd.12786

A. J. Deegan et al. Optical coherence tomography angiography monitors human cutaneous wound healing over time. *Quant Imaging Med Surg* 2018; 8(2):135-150

WO2008/053194—Compounds Which Potentiate AMPA Receptor And Uses Thereof In Medicine. Application No. PCT/EP2008/053194.

Ronneberger O., Fischer P., Brox T. (2015) U-Net: Convolutional Networks for Biomedical Image Segmentation. In: Navab N., Hornegger J., Wells W., Frangi A. (eds) Medical Image Computing and Computer-Assisted Intervention—MICCAI 2015. MICCAI 2015. Lecture Notes in Computer Science, vol 9351. Springer, Cham. https://doi.org/10.1007/978-3-319-24574-4_28

Goodfellow, Ian; Pouget-Abadie, Jean; Mirza, Mehdi; Xu, Bing; Warde-Farley, David; Ozair, Sherjil; Courville, Aaron; Bengio, Yoshua (2014). Generative Adversarial Networks (PDF). Proceedings of the International Conference on Neural Information Processing Systems (NIPS 2014). pp. 2672-2680.

Zhou, Zongwei, et al. "Unet++: A nested u-net architecture for medical image segmentation." *Deep learning in medical image analysis and multimodal learning for clinical decision support*. Springer, Cham, 2018. 3-11.

Dolz, Jose, Ismail Ben Ayed, and Christian Desrosiers. "Dense multi-path U-Net for ischemic stroke lesion segmentation in multiple image modalities." *International MICCAI Brainlesion Workshop*. Springer, Cham, 2018.

Zhang, Zizhao, Lin Yang, and Yefeng Zheng. "Translating and segmenting multimodal medical volumes with cycle- and shape-consistency generative adversarial network." *Proceedings of the IEEE conference on computer vision and pattern Recognition.* 2018.

Kazeminia, Salome, et al. "GANs for medical image analysis." *Artificial Intelligence in Medicine* (2020): 101938.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Various modifications and variations of the described compositions, methods, and uses of the technology will be apparent to those skilled in the art without departing from the scope and spirit of the technology as described. Any sub-titles herein are included for convenience only, and are not to be construed as limiting the disclosure in any way.

Unless defined otherwise, all technical and scientific terms used herein have the same meaning as commonly understood by one of ordinary skill in the art to which this disclosure is related. For example, the *Concise Dictionary of Biomedicine and Molecular Biology*, Juo, Pei-Show, 2nd ed., 2002, CRC Press; *The Dictionary of Cell and Molecular Biology,* 3rd ed., 1999, Academic Press; and the *Oxford Dictionary of Biochemistry and Molecular Biology*, Revised, 2000, Oxford University Press, provide one of skill with a general dictionary of many of the terms used in this disclosure.

The methods of any embodiments described herein may be provided as computer programs or as computer program products or computer readable media carrying a computer program which is arranged, when run on a computer, to perform the method(s) described above.

Unless context dictates otherwise, the descriptions and definitions of the features set out above are not limited to any particular aspect or embodiment of the invention and apply equally to all aspects and embodiments which are described.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%. Units, prefixes, and symbols are denoted in their Système International de Unites (SI) accepted form. Numeric ranges are inclusive of the numbers defining the range.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

Other aspects and embodiments of the invention provide the aspects and embodiments described above with the term "comprising" replaced by the term "consisting of" or "consisting essentially of", unless the context dictates otherwise.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

The invention claimed is:

1. A method of assessing a wound in a subject, the method comprising:

receiving, by a processor, one or more optical coherence tomography images of the wound; and analyzing, by said processor, the one or more optical coherence tomography images using a deep learning model that has been trained to classify pixels in an optical coherence tomography image of a wound between a plurality of classes comprising a plurality of classes associated with different types of wound tissue, thereby obtaining for each image analyzed, an indication of the location of tissue likely to belong to each of the different types of wound tissue in the respective image, wherein the plurality of classes associated with different types of wound tissue comprise at least a class associated with neoepidermis, a class associated with clot tissue and a class associated with granulation tissue, and said processor analyzing the one or more optical coherence tomography images of the wound using the deep learning model comprises said processor obtaining for each image analyzed an indication of the location of likely neoepidermis, likely clot tissue and likely granulation tissue in the respective image, wherein the plurality of classes further comprise one or more classes selected from: a class associated with intact tissue, and a class associated with background.

2. The method of claim 1, wherein:

the method further comprises said processor training said deep learning model using a plurality of training optical coherence tomography images, wherein areas of each training image showing visual features indicative of the presence of the different types of wound tissues are labelled accordingly; and/or the deep learning model takes as input a single image and analyzing the one or more optical coherence tomography images comprises providing each of the one or more optical coherence tomography images individually as input to the deep learning model.

3. The method of claim 1, wherein the indication of tissue likely to belong to each of the different types of wound tissue in the respective image is obtained by said processor as one or more segmentation maps, wherein a segmentation map is an image of the same size as the image analyzed, with pixels classified in a particular class assigned a different value from pixels that have not been classified in the particular class.

4. The method of claim 1, wherein:

each optical coherence tomography image of the wound shows signal from the surface of the skin of the subject to a maximum depth.

5. The method of claim 4, wherein the maximum depth is between 1 and 2 mm.

6. The method of claim 1, wherein the deep learning model is a convolutional neural network, and/or wherein the deep learning network is a u-net or a generative adversarial network, and/or wherein the deep learning network comprises a contracting path that reduces spatial information and increases feature information, and an expansive path that combines features and spatial information.

7. The method of claim 1, further comprising said processor applying one or more post-processing steps to the output of the deep learning model, wherein the post-processing steps comprise one or more of: smoothing the boundaries of the areas comprising pixels identified as belonging to one or more classes, and re-labelling pixels identified as belonging to one or more classes where the pixels satisfy one or more criteria applying to the neighboring pixels.

8. The method of claim 1, further comprising said processor determining, using the output from the deep learning model, the surface area corresponding to the pixels identified by the deep learning model as likely to belong to at least one of the different types of wound tissue in the one or more images, and the at least one type of wound tissue is selected from the group consisting of: neoepidermis, clot tissue, and granulation tissue.

9. The method of claim 1, further comprising:

the processor determining the volume of at least one of the different types of wound tissue in the wound, by:

analyzing a plurality of images of optical coherence tomography images of the wound using the deep learning model;

determining, using the output from the deep learning model, for each of the plurality of images, the surface area corresponding to the pixels identified as likely to belong to the respective one of the different types of wound tissue, such as the surface area corresponding to the pixels identified as likely neoepidermis, the surface area corresponding to the pixels identified by the deep learning model as likely clot tissue, and/or the surface area corresponding to the pixels identified by the deep learning model as likely granulation tissue; and multiplying the determined surface area(s) in each image by a predetermined distance.

10. The method of claim 1, wherein the subject is a human subject and/or wherein the wound is a skin wound, and/or wherein the wound is a traumatic wound, a surgical wound, or a skin ulcer.

11. A system for automated assessment of wound tissue, the system comprising: at least one processor, and at least one non-transitory computer readable medium containing instructions that, when executed by the at least one processor, cause the at least one processor to perform the method of claim 1.

12. The system of claim 11, wherein the system further comprises optical coherence tomography imaging means in communication with the processor.

13. A method for the treatment or prophylaxis of wounds in a patient susceptible to develop chronic wounds, comprising assessing the wound using the method of claim 1.

14. The method of claim 13, wherein the method comprises repeating the step of assessing the wound of the patient after a period of time and/or after administering to said patient a therapeutically effective amount of a compound or composition for the treatment of wounds, and/or wherein the method comprises adjusting a course of treatment of the patient depending on the results of the assessment of the wound.

15. A non-transitory computer readable medium comprising instructions that, when executed by at least one processor, cause the at least one processor to perform the method of claim 1.

16. The method of claim 1, wherein the plurality of classes associated with different types of wound tissue further comprise a class associated with collagen and/or a class associated with liquid blood and wherein analyzing the one or more optical coherence tomography images of the wound using the deep learning model further comprises obtaining for each image analyzed an indication of the location of likely collagen and/or likely liquid blood in the respective image.

17. The method of claim 1, wherein the plurality of classes consists of classes associated with each of neoepidermis, clot tissue, granulation tissue, liquid blood, collagen, intact tissue and background.

18. The method of claim 1, wherein a plurality of optical coherence tomography images of the wound are received and analyzed by said processor, together forming a stack of images that show signal across an area of the surface of the skin of the subject.

19. The method of claim 18, wherein the method further comprises the processor combining the indications of the location of the tissue likely to belong to each of the different types of wound tissue, in the respective images to obtain a three-dimensional map of the location of tissue likely to belong to each of the different types of wound tissue.

20. The method of claim 1, further comprising the processor determining the width of the wound based on a dimension of the location(s) of tissue identified as likely to belong to one or more of the different types of wound tissue in at least one of the one or more images.

21. The method of claim 20, wherein the one or more of the different types of wound tissue include neoepidermis, clot and granular tissue.

* * * * *